United States Patent
Waxman et al.

(10) Patent No.: US 10,190,976 B2
(45) Date of Patent: *Jan. 29, 2019

(54) SCANNING IR SENSOR FOR GAS SAFETY AND EMISSIONS MONITORING

(71) Applicant: MultiSensor Scientific, Inc., Somerville, MA (US)

(72) Inventors: Allen M. Waxman, Newton, MA (US); Jason M. Bylsma, Boston, MA (US); Allan Vaitses, Marion, MA (US)

(73) Assignee: MultiSensor Scientific, Inc., Somerville, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/923,794

(22) Filed: Mar. 16, 2018

(65) Prior Publication Data

US 2018/0266944 A1 Sep. 20, 2018

Related U.S. Application Data

(60) Provisional application No. 62/472,463, filed on Mar. 16, 2017, provisional application No. 62/587,304, filed on Nov. 16, 2017.

(51) Int. Cl.
| | | |
|---|---|---|
| *G01N 21/35* | (2014.01) | |
| *G01N 21/3518* | (2014.01) | |
| *G01F 1/76* | (2006.01) | |
| *G01N 21/3504* | (2014.01) | |
| *G01M 3/38* | (2006.01) | |

(52) U.S. Cl.
CPC ........... *G01N 21/3518* (2013.01); *G01F 1/76* (2013.01); *G01M 3/38* (2013.01); *G01N 2021/3513* (2013.01)

(58) Field of Classification Search
CPC .............................. G01N 21/3518; G01F 1/76
See application file for complete search history.

(56) References Cited

U.S. PATENT DOCUMENTS

| | | |
|---|---|---|
| 3,662,171 A | 5/1972 | Brengman et al. |
| 4,490,613 A | 12/1984 | Brame |

(Continued)

FOREIGN PATENT DOCUMENTS

WO WO-2017/201194 A1 11/2017

OTHER PUBLICATIONS

Benson, R. et al., Standoff passive optical leak detection of volatile organic compounds using a cooled InSb based infrared imager, Proceedings of the Air & Waste Management Assoc. Conf. Extended Abstract No. 06-A-131-AQMA, pp. 1-10 (2006).

(Continued)

*Primary Examiner* — Michael C Bryant
(74) *Attorney, Agent, or Firm* — Choate, Hall & Stewart LLP; William R. Haulbrook; Ronen Adato

(57) ABSTRACT

Apparatus and methods for rapidly detecting, localizing, imaging, and quantifying leaks of natural gas and other hydrocarbon and greenhouse gases. Scanning sensors, scan patterns, and data processing algorithms enable monitoring a site to rapidly detect, localize, image, and quantify amounts and rates of hydrocarbon leaks. Multispectral shortwave infrared detectors sense non-thermal infrared radiation from natural solar or artificial illumination sources by differential absorption spectroscopy. A multispectral sensor is scanned to envelop an area of interest, detect the presence and location of a leak, and raster scan the area around the leak to create an image of the leak. The resulting absorption image related to differential spectral optical depth is color mapped to render the degree of gas absorption across the scene. Analysis of this optical depth image, with factors including known inline pressures and/or surface wind speed measurements, enable estimation of the leak rate, i.e., emission mass flux of gas.

7 Claims, 18 Drawing Sheets
(12 of 18 Drawing Sheet(s) Filed in Color)

Mass Flow Estimation in Wind for Round Hole Orifices

(56) References Cited

U.S. PATENT DOCUMENTS

| | | | | |
|---|---|---|---|---|
| 4,543,481 | A | * | 9/1985 | Zwick .................... G01M 3/38 250/338.5 |
| 4,864,127 | A | | 9/1989 | Brame |
| 5,103,675 | A | * | 4/1992 | Komninos .............. G01M 3/24 381/98 |
| 5,281,816 | A | | 1/1994 | Jacobson et al. |
| 5,306,913 | A | | 4/1994 | Noack et al. |
| 5,656,813 | A | | 8/1997 | Moore et al. |
| 6,680,778 | B2 | | 1/2004 | Hinnrichs et al. |
| 6,690,472 | B2 | | 2/2004 | Kulp et al. |
| 7,075,653 | B1 | | 7/2006 | Rutherford |
| 7,649,174 | B2 | | 1/2010 | Mammen et al. |
| 7,977,639 | B2 | | 7/2011 | Maillart et al. |
| 8,193,496 | B2 | | 6/2012 | Furry |
| 8,426,813 | B2 | | 4/2013 | Furry |
| 2006/0202122 | A1 | | 9/2006 | Gunn et al. |
| 2006/0203248 | A1 | | 9/2006 | Reichardt et al. |
| 2010/0231722 | A1 | | 9/2010 | Hill, Jr. et al. |
| 2013/0327942 | A1 | | 12/2013 | Silny |
| 2014/0008526 | A1 | | 1/2014 | Zeng et al. |
| 2014/0160479 | A1 | * | 6/2014 | Hager ................ G01N 21/3504 356/438 |
| 2015/0069239 | A1 | | 3/2015 | Kester et al. |
| 2015/0316473 | A1 | * | 11/2015 | Kester ...................... G06K 9/22 250/339.02 |
| 2015/0323449 | A1 | * | 11/2015 | Jones ................ G01N 21/3103 356/437 |
| 2016/0069743 | A1 | | 3/2016 | McQuilkin et al. |
| 2016/0131576 | A1 | | 5/2016 | Cabib et al. |
| 2016/0349228 | A1 | * | 12/2016 | Kester ................... G01J 5/0896 |
| 2017/0234761 | A1 | * | 8/2017 | Augusto ................ G01M 3/38 250/338.5 |
| 2017/0336281 | A1 | | 11/2017 | Waxman et al. |

OTHER PUBLICATIONS

Buchwitz, M. et al., Atmosphere methane and carbon dioxide from SCIAMACHY satellite data, Atmos. Chem. Phys., 5:941-962 (2005).

Byer, R. L. and Shepp, L. A., Two-dimensional remote air-pollution monitoring via tomography, Optics Letters, 4(3):75-77 (1979).

Clark, R. N. et al., Reflectance spectroscopy of organic compounds: Alkanes, J. Geophysical Research, 114:E030001:1-19, (2009).

Epperson, D. et al., Equivalent Leak Definitions for Smart LDAR (Leak Detection and Repair) When Using Optical Imaging Technology, Journal of the Air & Waste Management Association, 57(9):1050-1060, (2007).

Furry, D. et al., Detection of Volatile Organic Compounds (VOC's) with a Spectrally Filtered Cooled Mid-Wave Infrared Camera, Inframation Proceedings, Document No. ITC 108A 2005-06-01, 6 pages, (2005).

Gottwald, M. et al., The Instrument, Chapter 3 in SCHIAMACHY— Exploring the Changing Earth's Atmosphere, pp. 29-46, (2006).

Gross, W. et al., Localization of Methane Distributions by Spectrally Tuned Infrared Imaging, SPIE, Part of the SPIE Conference on Air Monitoring and Detection of Chemical and Biological Agents, 3533:234-240, (1998).

Inada, H. et al., Uncooled SWIR InGaAs/GaAsSb type II quantum wells focal plane array, Proc. of SPIE, Infrared Technology and Applications XXXVI, 7660:76603N-1-76603N-7 (2010).

International Search Report and Written Opinion, International Application No. PCT/US2017/033157 (Hydrocarbon Leak Imaging and Quantification Sensor, filed May 17, 2017), issued by ISA/US, Commissioner for Patents, 12 pages, Sep. 14, 2017.

International Search Report, International Application No. PCT/US18/22943 (Scanning IR Sensor for Gas Safety and Emissions Monitoring, filed Mar. 16, 2018), issued by ISA/US, Commissioner for Patents, 4 pages, Aug. 8, 2018.

Shulz, M. et al., High-resolution thermophysical measurements using staring infrared detector arrays, High Temperatures—High Pressures, 32:547-556 (2000).

Van Den Bosch, C. J. H. and Duijm, N. J., Overflow and Spray release, Chapter 2, Methods for Calculation of Physical Effects: Due to Release of Hazardous Materials (Liquids & Gases)., Eds: Van den Bosch et al., 3rd Ed. 2nd Printing, CPR 14E, TNOx—The Netherlands Organization of Applied Scientific Research, pp. 2.1-2.179 (2005).

Written Opinion, International Application No. PCT/US18/22943 (Scanning IR Sensor for Gas Safety and Emissions Monitoring, filed Mar. 16, 2018), issued by ISA/US, Commissioner for Patents, 9 pages, Aug. 8, 2018.

\* cited by examiner

5-Element Array of Discrete Photo-Detectors
With a 5-Band Spectral Filter Overlay 9-Element Array of Macro-Pixel Photodiodes
Covered by a 9-Band Spectral Filter Mosaic Sensor & Illuminator Mounted on a Pan-Tilt Unit atop a Mast, Scanning Overtop a Wellpad, Creates an Optical Sheath that Envelopes the Entire Site Plan View of Square Site Full Coverage "Emissions"
Polar Raster Scan Pattern Relative to Sensor S

Plan View of Square Site with "Safety" Monitoring
Boundary Scan Pattern Relative to Sensor S Plan View of Square Site with "Localization"
Scan Pattern and Sub-Sector Partition (red)

Plan View of Square Site with
Shifted (red) Sub-Sector Raster Scan Pattern

Imaging Methane Emissions from Surface Patches

Imaging Methane Emissions from Wide-Area Surfaces

Methane Surface Patch Emission Geometry (Plan View)

Methane Wide-Area Surface Emission Geometry (Side View)

SCANNING IR SENSOR FOR GAS SAFETY AND EMISSIONS MONITORING

CROSS-REFERENCE TO RELATED APPLICATIONS

This application claims priority of U.S. Provisional Patent Application No. 62/472,463, filed Mar. 16, 2017 and U.S. Provisional Patent Application 62/587,304. filed Nov. 16, 2017.

STATEMENT REGARDING FEDERALLY SPONSORED RESEARCH OR DEVELOPMENT (Not Applicable)

SEQUENCE LISTING (Not Applicable)

BACKGROUND OF THE INVENTION

This invention consists of sensors and algorithms to scan a site containing natural gas and related infrastructure, and automatically detect, localize, image and quantify hydrocarbon gas leaks using a short-wave infrared radiation detector in combination with multiple spectral filters under natural solar or artificial illumination. Particular embodiments recited address detection and quantification of methane gas leaks. Quantification includes total volume, total mass, and emission/leak rates of methane and other gases of interest. The invention is suitable for both gas safety (rapid detection) and emissions monitoring applications. Several embodiments described support applications to installed fixed site monitoring, relocatable work site monitoring, and hand portable site inspection. These and similar embodiments are applicable more generally to hydrocarbon gases, liquids, emulsions, solids, and particulates, toxic gases, and key greenhouse gases.

Natural gas leaks create both safety and environmental hazards, and occur along the entire gas supply chain from the well to the street (so-called upstream, midstream, and downstream sectors). Methane, the primary constituent of natural gas is combustible in air, and is also a potent greenhouse gas. Other hydrocarbons found in natural gas, as well vapors emanating from liquids separated from gas and oil include ethane, propane, butane, pentane, hexane, octane, and heavier hydrocarbons, which form volatile organic compounds that generate smog which is a health hazard. Thus, there are compelling reasons to detect leaks of methane gas and other hydrocarbon gases, so that such leaks can be repaired. However, in order to repair such leaks, it is necessary to also localize the leak, and in order to prioritize repairs it is desirable to quantify the leak in terms of leak rate or emission flux. Estimating gas emission flux is also needed to assess environmental impact of greenhouse gases. Moreover, it is desirable to have a means to monitor or inspect wide areas for such leaks and do so quickly from a safe and practical standoff distance, while maintaining the ability to pinpoint the leak location and estimate the leak rate. It is also desirable to conduct effective leak monitoring in the presence of naturally occurring ambient gases and vapors, such as water vapor, and regardless of the relative temperature between leaked gas and the background environment. A cost-effective solution is also necessary if such solutions are to be broadly adopted and utilized.

Gas detectors can be classified according to their coverage extent, as either spot sensors, line sensors or area sensors. Spot sensors, often referred to as sniffers, draw in a local sample of air and detect the presence of a combustible or toxic gas by means of various analytical methods. They can be fixed in place for continuous monitoring, or hand portable for inspections, but they require direct sampling in place and provide very limited coverage. They may provide concentration measurements, but do not provide leak rate estimates. Other instrumentation is available to locally sample (as opposed to image) known leaks in order to provide an estimate of leak rate, but they too provide only local coverage and require direct collection of gas from the leaking component.

Optical line sensors, also known as open-path gas detectors, employ optical means to detect gas that lies along the line between a dedicated light emitter (e.g., laser, tunable laser, or narrowly focused broadband source) and a dedicated photo-detector (or multiple photo-detectors). Such detectors exploit the absorption of light (typically in different parts of the infrared spectrum) at select wavelengths characteristic of the molecular composition of the gas of interest. These sensors detect gas present anywhere along the line between the light emitter and the photo-detector (or between combined emitter/detector assembly and a remote reflector if the optical path is folded), but they cannot determine where along the path the gas is, nor from where it came, and has limited coverage to only the narrow open path between emitter and detector. By utilizing multiple wavelengths of light, such sensors can measure column density of gas along the open path, but cannot measure or estimate concentration nor leak rate. Open-path sensors can be installed in place, hand portable, or mobile aboard ground and air vehicles. In order to achieve area coverage from a standoff distance, it is recognized that imaging sensors offer many advantages over spot and line sensors, in that they can detect the presence of gas and possibly localize the leak source.

Several gas imaging technologies have been proposed, developed, patented, and are commercially available. They are all based on the absorption of infrared light at wavelengths characteristic of the molecules of interest. For methane and hydrocarbons in general, most imagers operate in select bands of the mid-wave infrared and long-wave infrared spectrum. The leading commercially available gas imaging sensors operate in only a single narrow band of the mid-wave infrared spectrum, and do not provide quantitative data, only pictures to be interpreted by the human operator. Other imaging sensors utilize multiple spectral bands in the long-wave infrared (the so-called "molecular fingerprint region") to detect and discriminate among different hydrocarbon gases, and to quantify the column density of gas at each pixel of the image. Such systems have proven to be both expensive and have significant shortcomings. These mid-wave and long-wave infrared sensors rely on thermally emitted light from the background to illuminate the gas that will absorb at select wavelengths as detected by the imaging sensors. This requires that the background and gas differ in temperature by at least several degrees Celsius, otherwise the light absorbed (or emitted) by the gas will not provide sufficient signal contrast to be reliably detected by the human operators of these thermal sensors. For example, in the case of surface emissions of natural gas due to an underground pipe leak, or methane emissions from a landfill, the gas percolates up through the soil and reaches thermal equilibrium with the soil by the time it emerges from the ground. Thus, there is little or no thermal contrast between the gas and the ground, and so cannot be reliably detected by a thermal infrared sensor. Another major shortcoming of mid-wave and long-wave gas imaging sensors is their poor performance in the presence of water vapor (high humidity, steam), fog and light rain. This is because the spectrum of water overlaps with key spectral features of methane in both the mid-wave and long-wave infrared spectral regions. Thus, water vapor will mask the presence of a methane leak, and conversely, water vapor will trigger a false alarm for methane. As both water vapor and methane are less dense than air, they both rise due to buoyancy and look alike in a spectrally filtered mid-wave or long-wave infrared image. Additionally, all mid-wave infrared and some long-wave infrared gas imaging sensors require cryogenic cooling, which is both expensive and unreliable. It is preferable to utilize only thermo-electric cooling to reduce dark current in gas imaging sensors. Finally, none of the available gas imaging sensors provides a capability to estimate leak rate from a hole, or emission flux from a surface. Some can provide column density of gas at each pixel, and using spatial information of the imaged gas jet, plume or cloud, one can then estimate local or average gas concentration.

In order to overcome the above-cited shortcomings of thermal infrared based imaging sensors for gas detection, it is possible to utilize differential absorption gas imaging in the short-wave infrared part of the spectrum. Atmospheric scientists using satellite-borne sensors like Landsat and SCIAMACHY have exploited this. It enables the detection of methane, other hydrocarbons, carbon dioxide, and other gases in the atmosphere based on molecular absorption of natural sunlight, without confusion of intervening water vapor. Such space-based imaging technologies provide synoptic scale maps of column densities of greenhouse gases and other air pollutants.

It is the purpose of this invention to provide sensors and methods that enable rapid gas leak detection and localization, imaging, and quantification of leak rate or emission mass flux, utilizing multispectral scan-based imaging in the short-wave infrared in combination with the hydrodynamics of turbulent gas jets and buoyant plumes. Multiple embodiments of the invention are described and have been developed, that are applicable more generally to natural gas and other hydrocarbon gases, liquids, emulsions, solids, and particulates, and to emissions monitoring of greenhouse gases such as methane and carbon dioxide.

BRIEF SUMMARY OF THE INVENTION

This invention describes apparatus and methods for detecting, localizing, imaging, and quantifying leaks of natural gas and other hydrocarbon and greenhouse gases, with application to both safety and emissions monitoring. It extends the apparatus and methods described in U.S. Provisional Patent Application 62/338,255, Hydrocarbon Leak Imaging and Quantification Sensor, filed 18 May 2016 by Waxman et al. of MultiSensor Scientific, Inc.

This invention describes scanning sensors, scan patterns, and data processing algorithms that enable monitoring a site of extended area, in order to rapidly detect, localize, image, and quantify amounts and rates of hydrocarbon leaks. A small number of multi spectral short-wave infrared detectors are used to sense non-thermal infrared radiation from natural solar or artificial illumination sources. More specifically, several embodiments of sensor systems are described that incorporate short-wave infrared detectors sensitive in the range of approximately 1.0 through 2.6 microns, in combination with approximately five spectral filters selected to create multiple spectral bands at least in the range of 1.9 to 2.5 microns, with respect to molecular spectral features associated with methane, ethane, propane, butane, carbon dioxide, and ammonia, while avoiding strong absorption features of water vapor. Detection is accomplished via absorption spectroscopy using natural sunlight or artificial illumination in direct transmission through a gas to the sensor, or reflected off a background surface with gas located between the background and the sensor.

The multispectral sensor can be scanned across a scene or an extended site using various scanning patterns designed to rapidly detect leaks, then localize the leaks, image them and quantify them in both volume (or mass of gas) and leak rate. Leaks can be detected, imaged and quantified, from pressurized pipelines, valves, and vessels above ground, as well as underground leaks as they emerge from the surface. The system can adapt to changing illumination conditions (brightness and spectrum) as well as changing background material reflectivity. Scanning can be accomplished using mechanical means involving a computer controlled precision pan-tilt unit, or using a combination of resonant vibrating mirrors, motor driven mirrors, and micro-machined mirror arrays.

The multispectral SWIR imagery is processed in real-time to yield an absorption image related to the differential spectral optical depth, or equivalently column density, of an intervening hydrocarbon gas such as methane, the major constituent of natural gas. Other hydrocarbon and greenhouse gases can be imaged simultaneously in the case of gas mixtures, as is typically the case. Recognition of individual constituent gases is accomplished using established pattern learning and recognition techniques commonly employed in multispectral and hyperspectral image processing.

The resulting absorption imagery is color mapped to render the degree of gas absorption across the scene, and overlaid on an optically registered color visible image that provides context. In the case of gas leaking from a hole or crack in a pressurized pipe, flange, valve or vessel, the escaping gas forms a turbulent jet or plume that is visible in the absorption image and from which the leak can be localized. The invented methods estimate both the diameter of the effective hole and the mass flux of leaking methane (or other gas) from the data present in this absorption image, if the internal pressure driving the leak is known approximately.

In the case of underground gas leaks, such as due to municipal gas infrastructure, the gas percolates through the subsurface soil and emerges at the surface, often in disconnected surface patches. These surface emissions diffuse into a thin layer next to the ground and rise (in the case of natural gas) due to buoyancy, but are quickly blown by ground-level winds. The invented methods estimate both the mass of gas and the mass flux from a surface patch by combining the absorption imagery with wind speed and direction measured near ground level. Estimation formulas are derived for the case of steady winds and gusting winds. The invention also addresses mass flux estimation from wide-area surface emissions, such as the case with large landfills or open pit mines and tailing ponds such as found in the Canadian oil sands region. When emissions occur over extended surfaces, a stratified methane atmosphere is established over the surface, with a buoyant vertical methane flux balanced by the surface emission flux. By sensing the absorption imagery from a known height/altitude above the surface, an estimate of surface methane emissions is established.

A real-time functional prototype of a leak imaging and quantification sensor has been built, and a graphical user interface that controls the sensor has been implemented on a touch-screen tablet display. Example imagery and data is shown in the figures. A similar scan imaging prototype is currently under development.

This invention has several key advantages over thermal infrared gas imaging sensors that operate in the mid-wave or long-wave infrared parts of the spectrum. This includes the ability to detect and quantify leaked gas with no temperature difference relative to the background, as the invention utilizes short-wave infrared light provided by natural sunlight or by lamps of appropriate color temperature, and does not rely on a thermal contrast between gas and the background or a background of varying temperature. The detectors suitable for use in this invention do not require cryogenic cooling, using instead thermo-electric cooling that is more reliable and less expensive than cryogenic coolers such as a Stirling engine or liquid nitrogen. The invention can also detect gas leaks in the presence of humid air, steam and fog, as the hydrocarbon features detected in the SWIR do not overlap spectral regions where water vapor absorption is significant, which is a major shortcoming for gas imagers operating in other parts of the infrared spectrum. The embodiment of a scan imager provides a cost-effective design, by allowing the use of a small number of discrete photo-diodes or small photodiode array. This approach trades away video-rate imaging for cost-effective but slower image scanning, which is satisfactory for numerous applications. Finally, the use of a rapid scanning device enables site-wide monitoring for gas leaks with a response time quick enough for safety applications (approximately 10 second response time). Many flexible scan patterns can be implemented and rapidly switched between in an automated fashion. This invention documents several examples of scan patterns to detect, localize and image leaks. These examples are meant to be illustrative but not exhaustive. Yet the concept and advantages should be clear. This enables the invention to be useful for gas safety, leak detection and repair, and gas emissions monitoring applications.

This invention and its various embodiments will be useful in detecting, localizing, imaging, and quantifying natural gas leaks from components along the entire gas supply chain, from the well head to compressors to transmission pipelines to gate stations and underground distribution networks. This invention has also been shown to be useful in detecting liquid oil spills on land, sand, seawater, and sea ice. Other embodiments of the invention will prove useful in detecting oil emulsions at sea and tar balls on beach. The embodiments of the invention described herein are suitable for packaging in the form of installed and relocatable fixed-site monitoring sensors, relocatable work-site safety sensors, and hand portable leak inspection sensors, all of which utilize small numbers of SWIR detectors and spectral filters in a scanning configuration.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Aspects of the described embodiments are more evident in the following description, when read in conjunction with the attached Figures.

DETAILED DESCRIPTION OF THE INVENTION

Figure 1A:
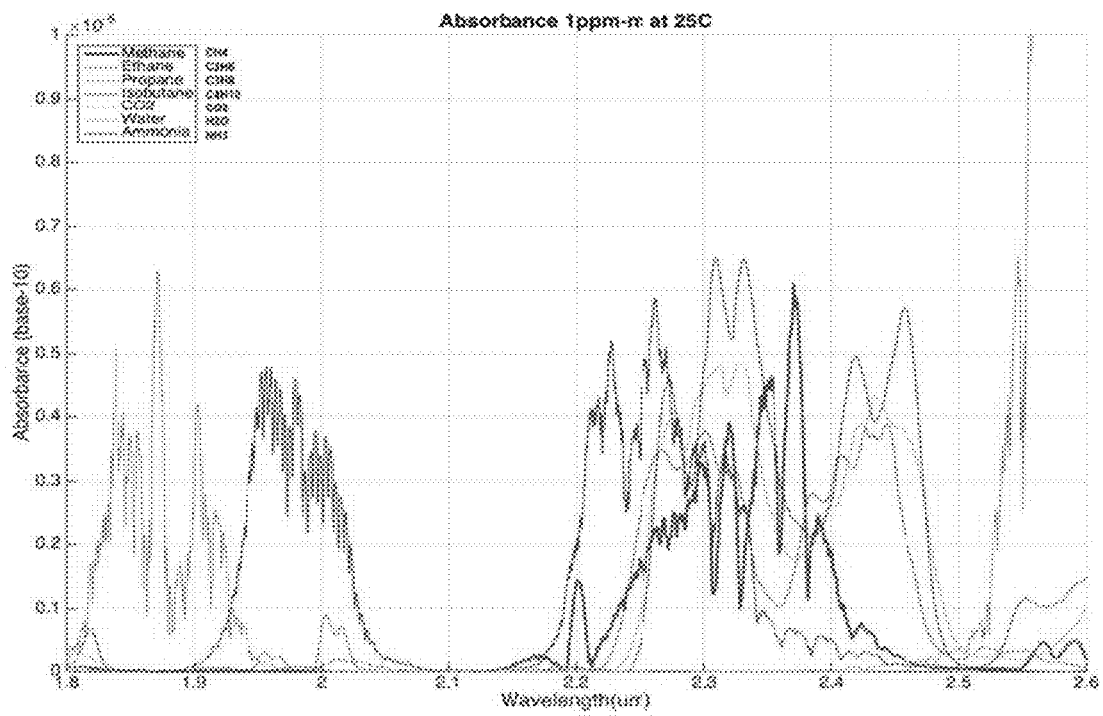
FIG. 1A illustrates the absorption spectra in the 1.9-2.6 micron range of the short-wave infrared for the gases methane, ethane, propane, butane, carbon dioxide, ammonia, and water vapor.

The mathematical methods that underlie this invention are described and build upon those described in U.S. Prov. Pat. Appl. No. 62/338,255. The description that follows may refer to methane as the gas of interest, though much of the formulation applies to other pure gases and gas mixtures except where positive buoyancy is assumed (and noted). The formulation may refer to the use of five spectral bands, however, this is only by way of example and not meant to be restrictive; this is a general multispectral formulation in the short-wave infrared. Indeed, many of the sensor designs and scanning concepts apply equally to other parts of the infrared spectrum, including mid-wave and long-wave infrared regions sometimes used for detecting gas leaks by absorption (or emission) of thermal radiation.

Principals of Gas Absorption Imaging

This invention detects gas leaks via differential absorption imaging spectroscopy in the range 1.9 to 2.6 microns, exploiting spectral features of hydrocarbons in the short-wave infrared (SWIR) region, primarily in the wavelength range of 2.0 to 2.5 microns. These wavelengths are not typically associated with those in the thermal emission regions of the mid-wave infrared (MWIR) and long-wave infrared (LWIR) for objects at terrestrial temperatures. Appreciable thermal emission at around 2.0 microns requires objects at temperatures of around 1200° C. Instead, this invention relies on illumination sources like natural sunlight and lamps of color temperature near 1200° C. Thus, the invention can detect hydrocarbons at the same temperatures as their backgrounds by using external illumination instead of thermally emitted light.

SWIR radiation from the sun or broadband artificial illumination, directly or in reflection off background objects, transmits through the ambient atmosphere, passes through a gas jet or plume emanating from a source such as for example a leak, continues towards the sensor where it is filtered into multiple spectral bands and detected on a photo-detector array that is sensitive to SWIR photons. Both the atmosphere and the gas absorb some of the light at wavelengths characteristic of the materials that comprise these media. In the case of natural gas the primary absorber is methane, while for the atmosphere the primary absorbers are water vapor and other ambient gases that may include methane as well as carbon dioxide. Incident light is also scattered out of the transmission path by particulates in the atmosphere and the gas leak itself. Light that is absorbed by the gas is subsequently reemitted in all directions, resulting in a reduction of light at characteristic wavelengths that is transmitted in the direction from the light source towards the sensor.

When imaging methane and other hydrocarbons, it is common to exploit their strong spectral features in the MWIR and LWIR, as the absorption in those spectral regions is greater than in the SWIR. However, it is important to consider the effects of water vapor absorption by the intervening atmosphere. In most applications, the physical extent of a gas jet, plume or cloud is small compared to the length of atmosphere that the light will propagate through on its way to the sensor. Thus, appreciable absorption may occur at wavelengths characteristic of water vapor, depending on the humidity of the air or the presence of fog or steam in optical field-of-view. It is therefore important to consider the relative absorption of methane to water vapor at the wavelengths that characterize methane. Despite the relatively weaker absorption cross-section for methane in the SWIR compared to the MWIR and LWIR, it has significantly higher absorption ratio to water vapor in the SWIR. Thus, for imaging gas in the presence of humidity or fog or steam, the SWIR region has particular advantage over both the MWIR and LWIR spectral regions. For many applications, this is an advantage, despite the lower absorption cross-section in the SWIR.

FIG. 1A shows a plot of absorption spectra from 1.8 to 2.6 microns range of the SWIR for the gases methane, ethane, propane, butane, carbon dioxide, ammonia, as well as for water vapor. From FIG. 2A it can be seen that the hydrocarbons possess broad feature complexes from 2.2 to 2.5 microns with much overlap in the range of 2.2 to 2.4 microns. Methane can be separated from the other hydrocarbons by its reduced absorption in the 2.4 to 2.5 micron range. It is also apparent that these gases have spectral features in the SWIR that lie between the strong water vapor features below 2.0 microns and above 2.5 microns. As is well known in the art, similar absorption features are present in the SWIR for liquid crude oil, oil-water emulsions, asphalt and tar.

Figure 1B:
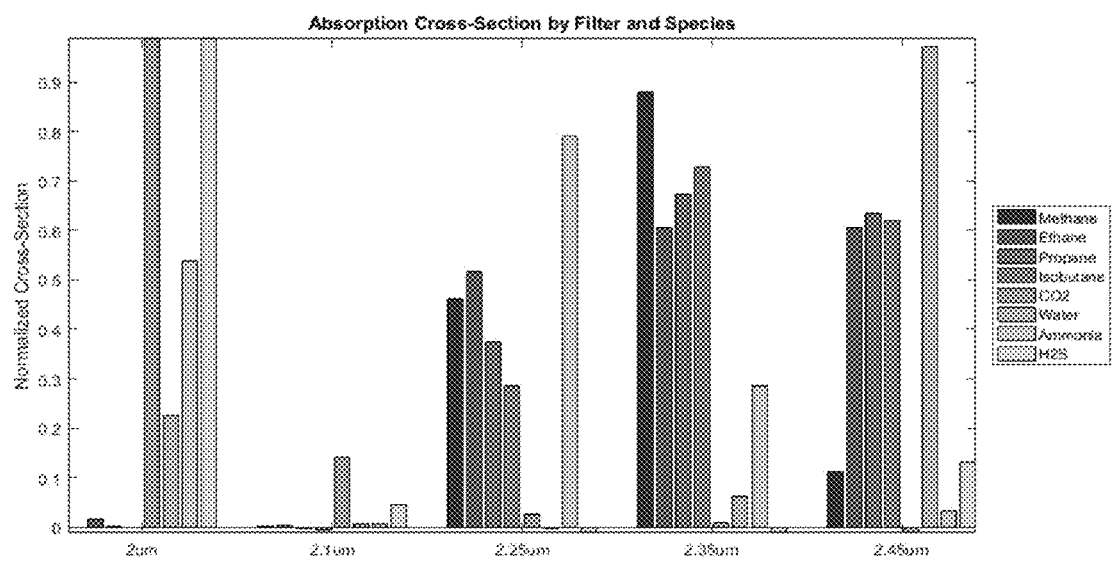
FIG. 1B illustrates normalized 5-band spectra for the same gases as in FIG. 1A, where the ideal spectral bands have bandwidths of 100 nanometers, and band centers at wavelengths of 2000, 2100, 2250, 2350, and 2450 nanometers.

Normalized 5-band spectra for the same gases are depicted in FIG. 1B. Here, the ideal spectral bands have bandwidths of 100 nanometers, and band centers at wavelengths of 2000, 2100, 2250, 2350, and 2450 nanometers.

The invention described here has been reduced to practice by building functional prototypes of a multispectral video imager and a scan imager for methane imaging, detection and quantification. The prototype dual-band video sensor images at 20 frames per second and displays gas absorption imagery overlaid on color visible imagery of the scene on a touch-screen user display. The prototype system is hand-portable and interfaces to external networks via both wireless and wired interfaces. The prototype 6-band scan sensor creates imagery of gas over a programmable and variable field-of-regard, by combining raster scanning with super-resolution image processing. The flexibility of switching among a variety of scan patterns enables this sensor to support both gas safety applications and emissions monitoring applications, in a cost-effective manner. This scan imager is suitable for mast-mounting to overlook wide-area installations, using a programmable pan-tilt unit to effect scanning. An alternative embodiment replaces the pan-tilt unit with scanning mirrors or a combination of scanning mirror and rotating optics, to enable compact packaging for a hand-portable gas imaging and quantification camera.

Imaging Sensor Embodiments

There are several different semiconductor materials that can be used to fabricate the basic photo-detector sensitive to the SWIR spectrum of light from approximately 1.8 to 2.6 microns, with a dark-current that can be suitably reduced by thermo-electric cooling. These include so-called extended-response indium gallium arsenide (extended-InGaAs) commonly grown on an indium phosphide (InP) lattice-mismatched substrate, and the recently developed type-II quantum wells made from alternating layers of InGaAs and gallium arsenide antiminide (GaAsSb) grown on an InP lattice-matched substrate. These two materials have different spectral response characteristics, but both can be used for detecting the hydrocarbons that comprise natural gas, and in particular, methane as well as VOCs. They also have different manufacturing yields due to their lattice structures. Thus, extended-InGaAs photo-detectors are only available as discrete photo-detectors and one-dimensional arrays but not as two-dimensional arrays, while type-II InGaAs/GaAsSb photo-detectors have been successfully fabricated and demonstrated as two-dimensional arrays. Mercury cadmium telluride (MCT) is a common infrared detector material that can also be used for imaging in the extended SWIR; however, its high dark-current requires cryogenic cooling with, for example, a Stirling engine to achieve useful signal-to-noise ratios.

All of the multi-spectral SWIR detector configurations described and shown herein may utilize scanning and focusing optics in order to create two-dimensional spectral imagery from which a gas detection imager can be created. As is known to one of ordinary skill in the art, all the disclosed detector embodiments lend themselves to packaging in hand-held systems, and can also be configured to operate on moving platforms such as ground vehicles, airborne rotor-craft and fixed-wing platforms, ships, rotating mast-mounted systems, translating rail-mounted systems, and orbiting satellites.

Figure 2A:
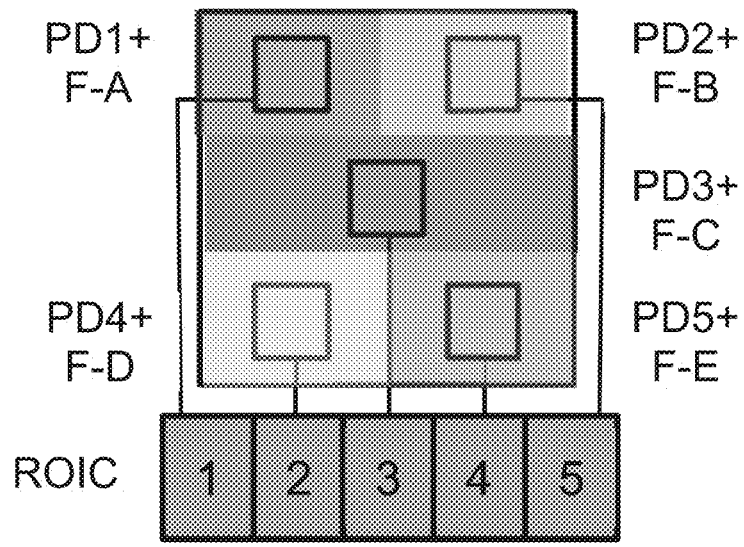
FIG. 2A illustrates a 5-element array of discrete photo-detectors with a 5-band spectral filter mosaic positioned over the photo-detector array.

FIG. 2A shows a 5-element array of discrete photo-detectors with a 5-band spectral filter mosaic positioned over the photo-detector array. Five discrete photo-detectors, PD1, PD2, PD3, PD4, and PD5, are arranged in a three row stack. Each photo-detector has a respective analog readout circuit and either dedicated or optionally shared analog-to-digital converter. Each photo-detector is covered with a separate spectral filter island, F-A, F-B, F-C, F-D, and F-E, respectively. In practice, the five discrete photo-detectors are to be mounted on a common thermo-electric cooler and enclosed in a hermetically sealed package with a transparent window. The spectral filters can be located outside the window aligned with the photo-detectors below, or be located on the inside of the window, or serve as the window itself. With the appropriate lens, this configuration forms the equivalent of a single multi-spectral SWIR pixel, or alternatively a small multispectral detector array. This configuration can clearly be extended to more or fewer discrete photo-detectors, each with its own spectral filter.

Figure 2B:
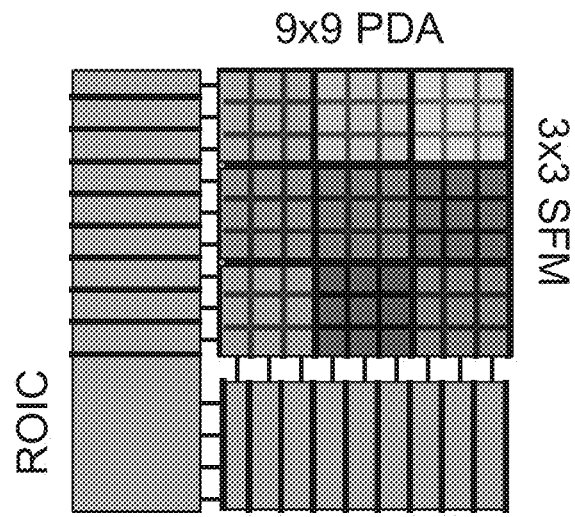
FIG. 2B illustrates the use of a small 9×9 element array of photo-detectors where sub-arrays of 3×3 detectors form macro-pixels each covered by a different spectral filter, where the filters are arranged in a 3×3 spectral filter mosaic.

FIG. 2B illustrates the use of a 9×9 element monolithic array of small photo-diode pixels where sub-arrays of 3×3 pixels form macro-pixels, each macro-pixel covered by a different spectral filter, and where the filters are arranged in a 3×3 spectral filter mosaic. While 3×3 pixel sub-arrays are illustrated, each filter island of the mosaic overlays a two-dimensional rectangular sub-array of small pixels. Upon readout of the entire detector array, each sub-array of pixels corresponding to the same filter island can be combined into a macro-pixel. This configuration trades off reduced spatial resolution for increased signal in a two-dimensional array of very small photo-detectors. Two-dimensional 2.5 um-SWIR type-II InGaAs/GaAsSb imaging arrays of various numbers of pixels, for example 64×64 pixels, can be adapted for use in the illustrated embodiment.

Gas Imaging Sensor System

Figure 3:
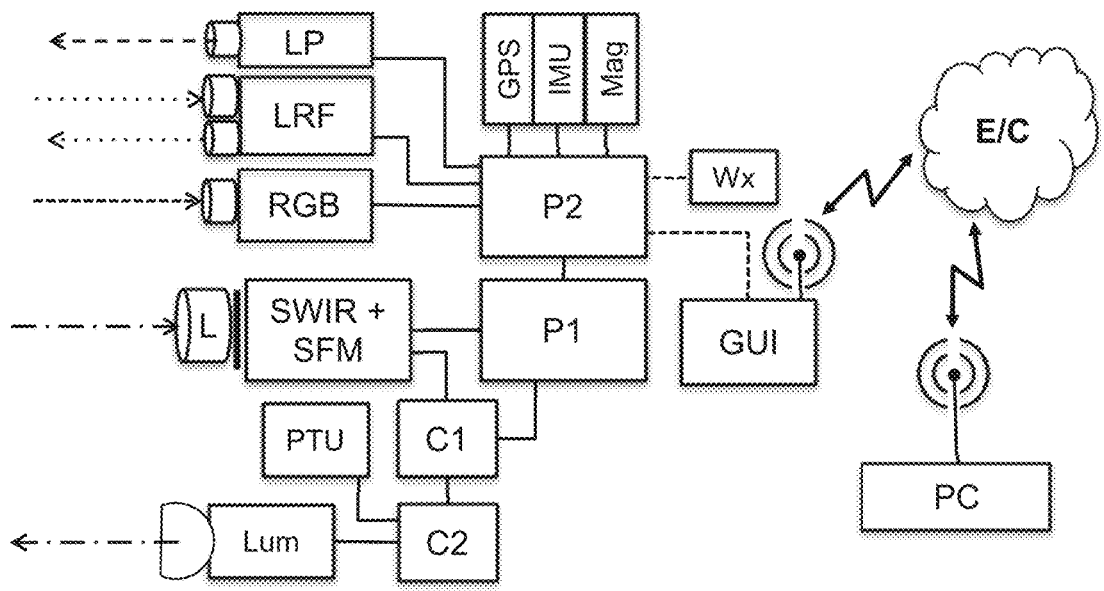
FIG. 3 is a system block diagram of the scanning sensor system for leak detection, localization, imaging, and quantification.

FIG. 3 is a system block diagram of a scanning sensor system for leak detection, localization, imaging, and quantification. The elements depicted within FIG. 3 are:

SWIR SWIR photo-detector array with read-out electronics;

SFM Spectral Filter Matrix located over the SWIR detector array;

L Lens for the SWIR photo-detector array, located in front of the SFM;

RGB Color Visible micro-camera with lens;

LRF Laser Range Finder (near IR);

LP Laser Pointer (visible "red dot");

PTU Pan-Tilt Unit for scanning sensors across a site in two dimensions;

Lum SWIR broadband illuminator to augment solar illumination;

C1 micro-Controller with A/D converter for sampling SWIR signals;

C2 micro-Controller for controlling PTU motion and illuminator brightness;

P1 micro-Processor #1 (real-time SWIR signal processor);

P2 micro-Processor #2 (all other sensors & GUI requests/display);

GPS Global Positioning System receiver;

IMU Inertial Measurement Unit (6 degrees of freedom);

Mag Magnetometer compass;

Wx Weather sensors (T, P, RH, wind speed & direction);

GUI Graphical User Interface on touchscreen tablet;

E/C Ethernet/Cloud; and

PC Personal computer remotely running the system via the cloud.

The discrete photo-detectors and spectral filter mosaic (SFM) of FIG. 2A or 2B form a single multispectral pixel by means of a defocusing lens (L), and this sensor is scanned across the scene in two directions by mounting it atop a high-accuracy pan-tilt unit (PTU) controlled by micro-Controller (C2). Alternatively, the discrete photo-detectors and spectral filter mosaic can be treated as a multispectral detector array, with lens (L) focusing the scene onto the array. The array is then scanned over the scene, and each spectral detector forms a spectral image, which must then be geometrically warped in order to register all spectral images to a common reference frame (e.g., at the center of the array). Alternative scanning mechanisms may be used to replace the high-accuracy pan-tilt unit, which may include mechanically positioned mirrors (e.g., galvanometer driven mirrors, resonant scanning mirrors, electrically-actuated micro-mirrors, rotary stage positioned mirrors, combinations of these mechanisms, and combinations of these mechanisms with a pan-tilt unit). Two-dimensional imagery is created by raster scanning across a desired, and possibly variable, field-of-regard. In order to create imagery of higher resolution than that obtained directly by scanning this sensor with its own narrow field-of-view, it is useful to employ spatial over-sampling in combination with super-resolution image processing, which is widely discussed in the literature. Two-dimensional scanning can also be accomplished in a compact configuration, for example, by a pair of scanning mirrors or a pair of rotating prisms. Two-dimensional imaging can also be achieved using a single scanning mirror combined with physical movement of the imaging sensor (e.g., translation or rotation in a direction perpendicular to the scan mirror motion) such as by mounting the sensor upon a moving platform (e.g., truck-mounted, airborne, rail-mounted, orbiting) or rotating the sensor in a mast-mounted configuration.

The imaging sensor system of FIG. 3 may also include one or more visible color (RGB) or black and white cameras, laser range finder (LRF) to measure distance from the sensor to a detected leak, global positioning system (GPS) sensor to determine sensor location (and indirectly leak location), inertial measurement unit (IMU) to sense linear and rotational accelerations including direction of gravity, magnetic sensor (Mag) to sense the earth's magnetic field acting as a compass, and/or weather sensors (Wx) to relay local atmospheric conditions including wind speed and direction, all of which is packaged together with one or more processors (P1, P2). The measured range to each (or select set of) SWIR sample(s) can be used to correct the parallax offset between that SWIR sample and its corresponding location in the visible RGB image, using the known spacing of the SWIR, RGB, and LRF sensors.

As shown in FIG. 3, one processor (P1) is associated with the multispectral SWIR camera and is responsible for real-time or near real-time processing of the SWIR multispectral data to create the gas absorption imagery. A separate processor (P2) has a path for accepting the visible camera (RGB) imagery and triggers the other low-bandwidth sensors (LRF, GPS, IMU, Mag). This processor (P2) also communicates wirelessly (or wired) with an external weather sensor (Wx) and a graphical user interface (GUI) implemented on a touch-screen tablet computer. The tablet, in turn, provides wireless access to an Ethernet or data cloud (E/C), which in turn can be accessed by a remote personal computer (PC). This arrangement enables remote (PC) access and control of one or more gas imaging sensor systems. Finally, an artificial illuminator (Lum) is controlled by a micro-controller (C2) and incorporated to enable gas imaging in the absence of sufficient sunlight or for indoor locations. Design concepts for scanning SWIR illuminators are described in U.S. Prov. Pat. Appl. No. 62/587,304, incorporated herein by reference. Alternative implementations are possible, such as for example (but not limited to) a configuration with:

the display or the controls or the complete user interface physically attached to the imaging device;

the display or the controls or the complete user interface physically remote from the imaging device;

the user interface implemented with physical knobs, buttons, sliders, dials, selectors or similar on the imaging device or separate from it;

the user interface implemented with digital representations of knobs, buttons, sliders, dials or similar using a display where this display can be either physically attached to the imaging device or connected by wired or wireless means;

a combination of physical and digital user interface described above;

processors P1 and P2 combined into a single processor or their functions distributed over multiple processors;

some or all of the low-bandwidth sensors being integrated into (a) the imaging device, (b) into a separate unit, or (c) into a display unit; and some or all of a single set of low-bandwidth sensors being connected to one or several processors that is (are) providing data for use by multiple imaging sensor systems.

Figure 4:
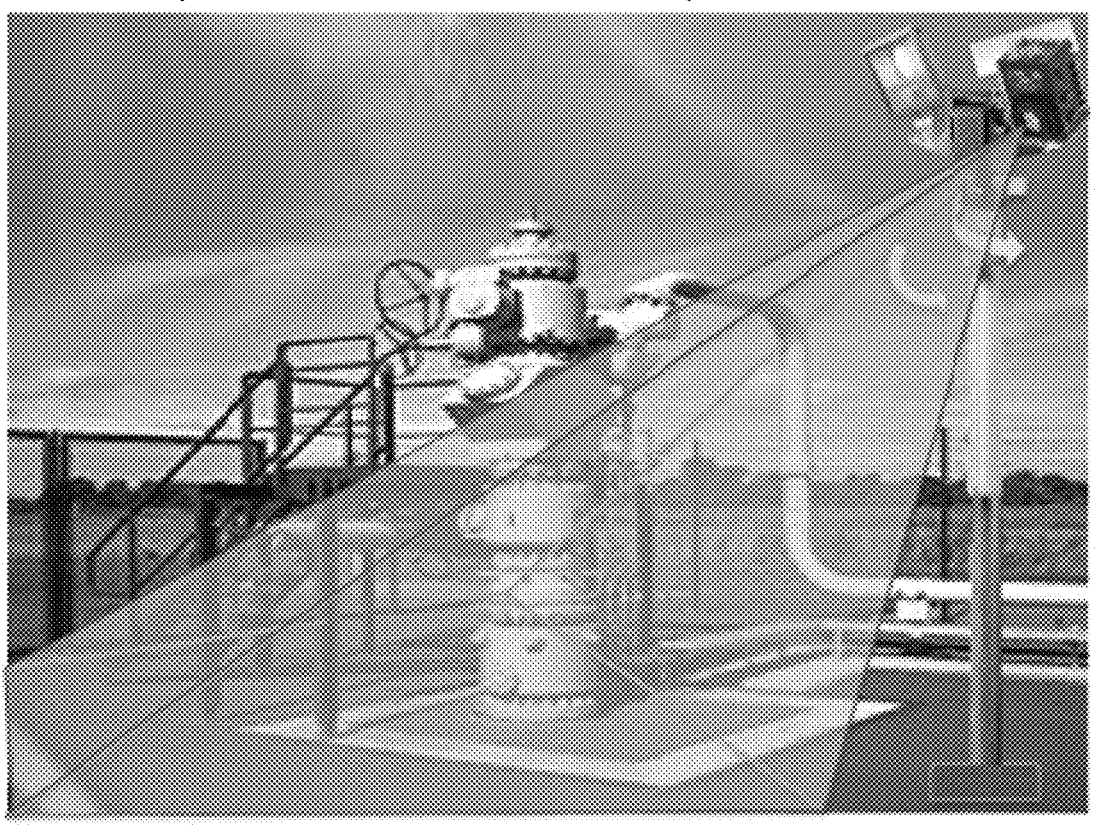
FIG. 4 illustrates the invention monitoring a gas wellpad, with the sensor and illuminator mounted on a pan-tilt unit atop a mast.

With the imaging sensor system of FIG. 3 properly calibrated, mounted atop a mast located next to a site of interest, such as illustrated in FIG. 4, the sensor can be scanned around the boundary of the site (in one embodiment, with an approximate size of 15 meters on a side) so as to create an optical sheath that envelops and covers the site and any equipment located upon the site. If a gas leak is present, the gas will migrate (due to buoyancy, wind, and diffusion) so as to cross some part of the optical sheath. This will result in selective absorption of the illumination within the multiple spectral bands, indicative of the particular species and amount of gas. Thus, a rapid boundary scan is used to detect the existence of a leak. Once so detected, a change of scan pattern is automatically triggered. The more focused scan pattern within the optical sheath enables localization of the leak on the site. Upon localizing the leak to within a predetermined extent, the scanning sensor automatically switches to a raster scan pattern of the area around the leak. By spatially oversampling the sensor data while scanning, a progressive-resolution image is constructed using super-resolution processing techniques. This results in a sequence of increasing resolution imagery around the leak, whereby the resolution of an image pixel exceeds the sampling resolution of the detector itself. Super-resolution image processing methods are well documented in the open literature.

In one embodiment shown in FIG. 4, a sensor and illuminator are mounted on a pan-tilt unit atop a mast, for example adjacent to a gas wellpad and having the well pad within a respective optical sheath monitored by the sensor. As the sensor scans a closed boundary of the site, it creates an optical sheath that envelopes the site.

Figure 5A:
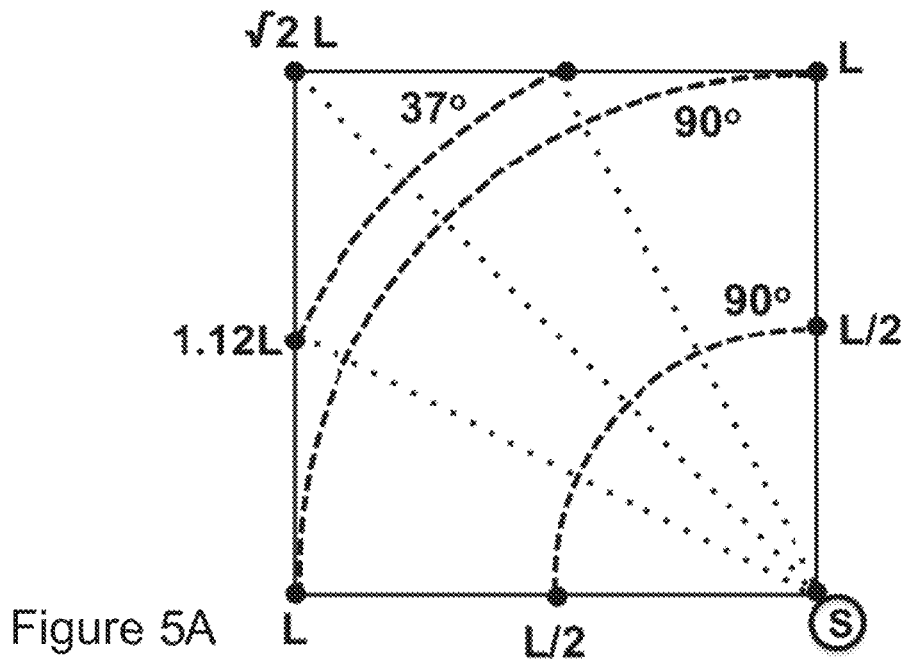
FIG. 5A diagrams a plan view of a square site of dimensions L×L (example L=10 meters) with the sensor S located at one corner of the site.

In FIG. 5A, a plan view is shown of a square site, such as the gas wellpad of FIG. 4, having dimensions of L×L. In an exemplary, non-limiting embodiment, L equals 10 meters. The sensor S is located at one corner of the site. As the sensor pans in angle across the site in azimuth, about a vertical axis of rotation, the line of sight of the sensor traces out polar arcs on the ground plane. As the sensor tilts in elevation, about a horizontal axis of rotation, the sensor line of sight traces radial lines on the ground plane.

Figure 5B:
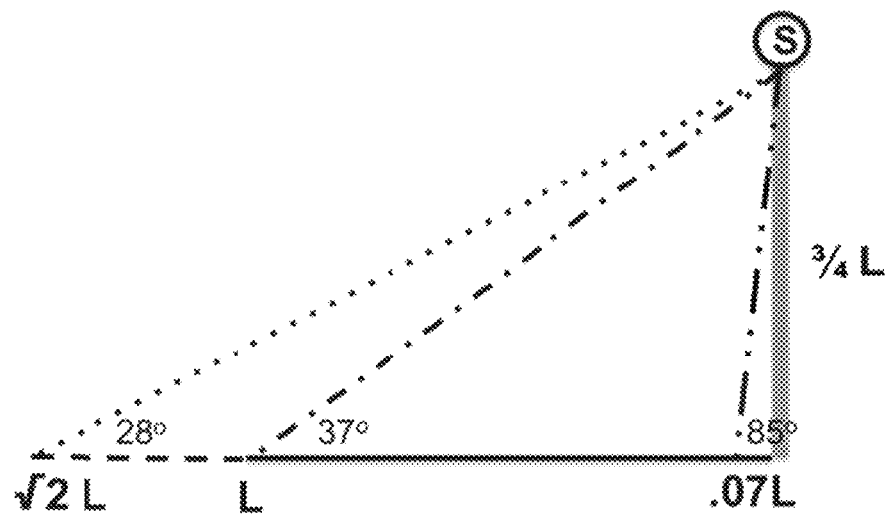
FIG. 5B diagrams a side view of the L×L square site, with sensor S mounted atop a mast of height ¾L located at one corner of the site.

With respect to FIG. 5B, a side view of an L×L site is presented. The sensor S is mounted atop a mast of height ¾L, disposed in one corner of the L×L site. Tilt angles relative to the horizontal are shown as rays from the sensor to various locations on the ground plane, including in the opposite corner of the site, at 28° from a horizontal plane extending from the sensor. Other exemplary rays are illustrated, including one intersecting the ground plane a distance L in the ground plane from the mast and 37° from horizontal, and one intersecting the ground plane a distance 0.07L in the ground plane from the mast and 85° from horizontal.

Figure 6:
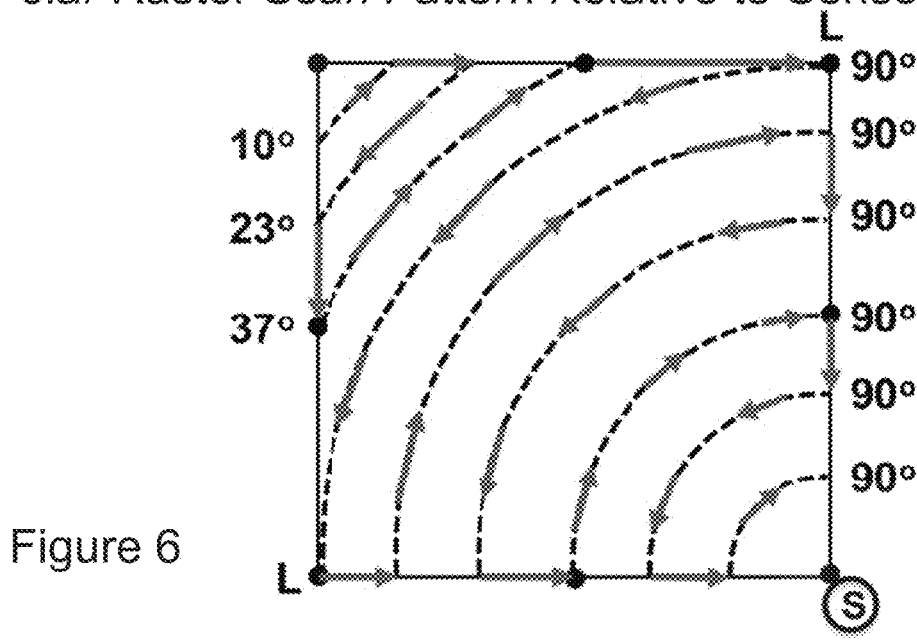
FIG. 6 illustrates a plan view of a square site covered by a polar coordinate raster scan pattern relative to the sensor S.

In FIG. 6, a square site, covered by a polar coordinate raster scan pattern relative to the sensor S, is presented in plan view. This raster scan pattern provides full coverage over the site and is suitable for monitoring gas emissions across the illustrated site. Such a polar scan provides multispectral imagery that can be super-resolved into high-resolution imagery for the detection and quantification of emissions from anywhere within the site.

Figure 7:
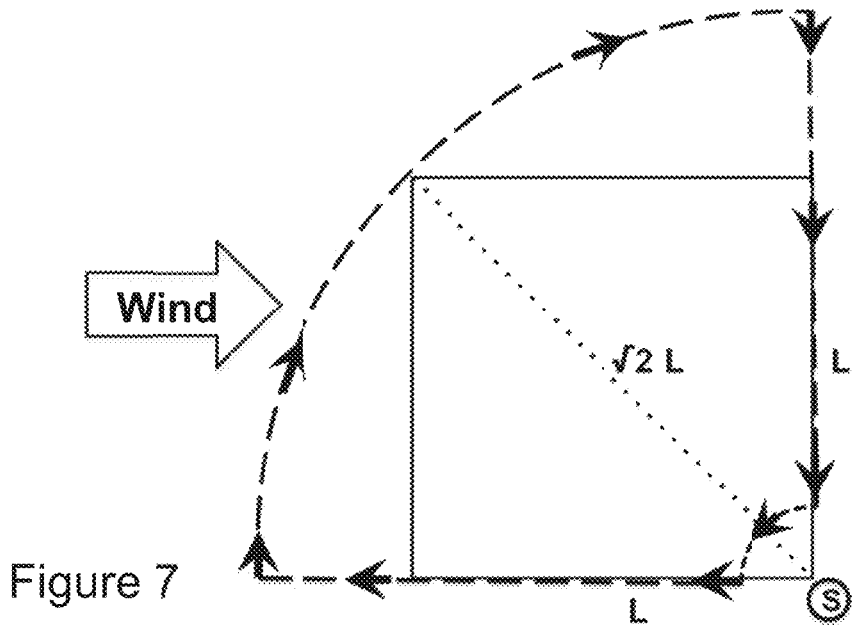
FIG. 7 illustrates a plan view of a square site with a boundary scan pattern relative to the sensor S.

A square site with a boundary scan pattern performed relative to a sensor S is illustrated in FIG. 7. This boundary scan can be performed rapidly to detect the presence of a gas leak somewhere within the site. Such a scan pattern is suitable for gas safety applications.

Figure 8:
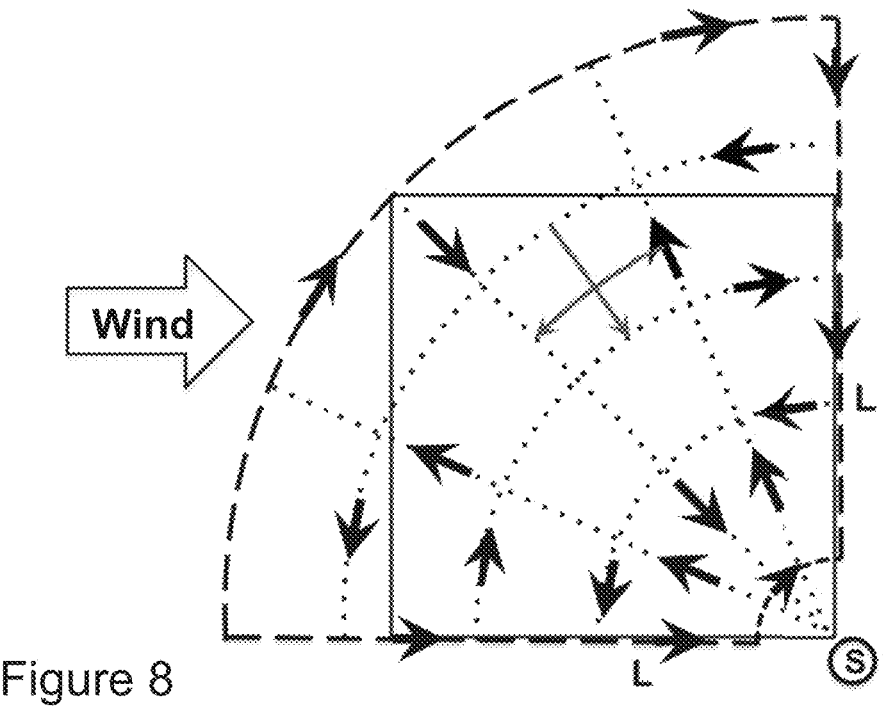
FIG. 8 illustrates a plan view of a square site with a localization scan pattern overlaid on the boundary scan pattern of FIG. 7.
Figure 9:
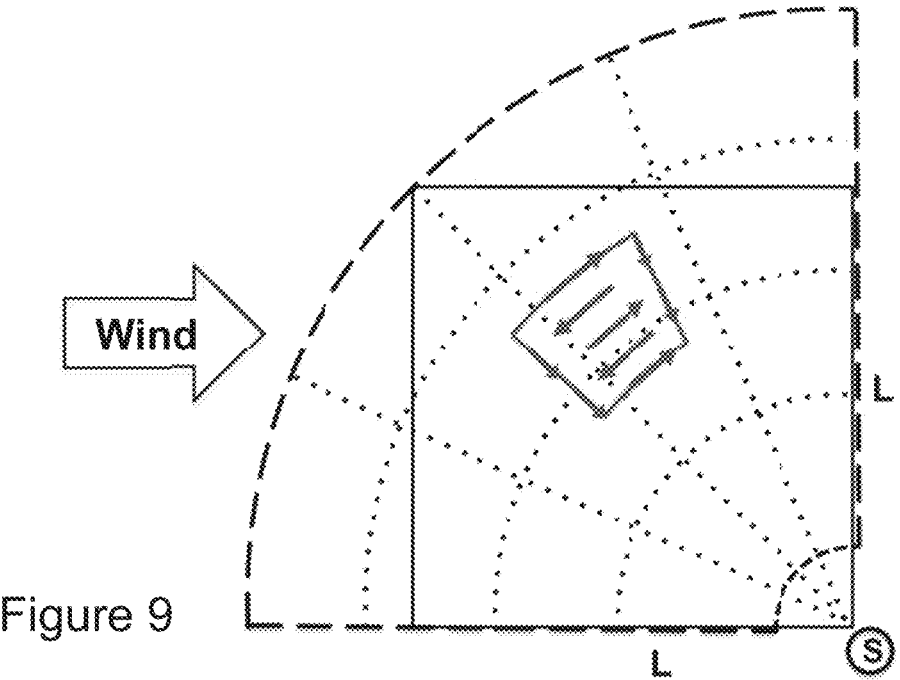
FIG. 9 illustrates a plan view of a square site with a local polar raster scan across a shifted sector within which the leak has been localized.

In FIG. 8, a plan view of a square site with a localization scan pattern overlaid on the boundary scan pattern of FIG. 7 is shown. This scan pattern divides the site into sectors, each with its own resulting optical sheath. This enables localization of a leak to within one of the sectors based on the measured wind direction. Further division of this sector into sub-sectors, as shown, localizes the leak, for example, to one quadrant of a sector. A shifted sector can then be defined about such an identified quadrant. For example, in FIG. 9, illustrated is a plan view of a square site having a local polar raster scan across the shifted sector within which a leak has been localized. The angular extent of the sector image is approximately 30×20 degrees in the illustrated example, or 500×400 milliradians.

Operation of Sensor Embodiments

Figure 10A:
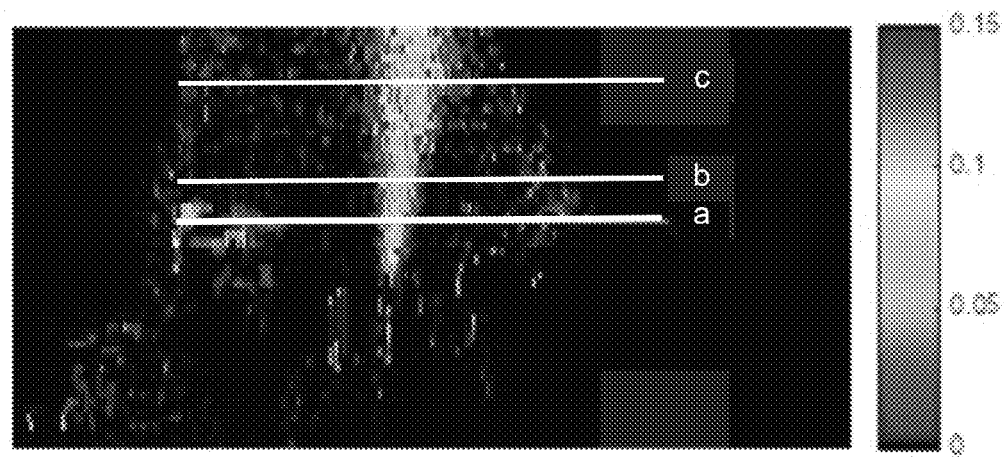
FIG. 10A shows a real-time absorption image of a methane gas jet exiting a 1 mm orifice from a test manifold pressurized to 1300 psig.

FIG. 10A illustrates a real-time absorption image of a methane gas jet exiting a 1 mm diameter round orifice with an internal pressure of 1300 psig (pounds per square inch—psi "gauge", i.e., relative to external atmospheric pressure of approximately 14.5 psi). The absorption image is colored according to a pixel-level differential optical depth scale shown to the right. This pixel-level differential optical depth is directly proportional to the number of methane molecules along each cone of rays between the light source and the photo-detector corresponding to each pixel; this is the so-called pixel column density of the gas. The turbulent structure of the jet is apparent near the top of the jet image. It is clear from the absorption image that the jet diameter grows linearly along the jet axis, as is consistent with the theoretical self-similar solution for turbulent jets. In this image, it is the noise level of the background differential optical depth that determines the boundary of the jet and so limits the visible diameter.

Figure 10B:
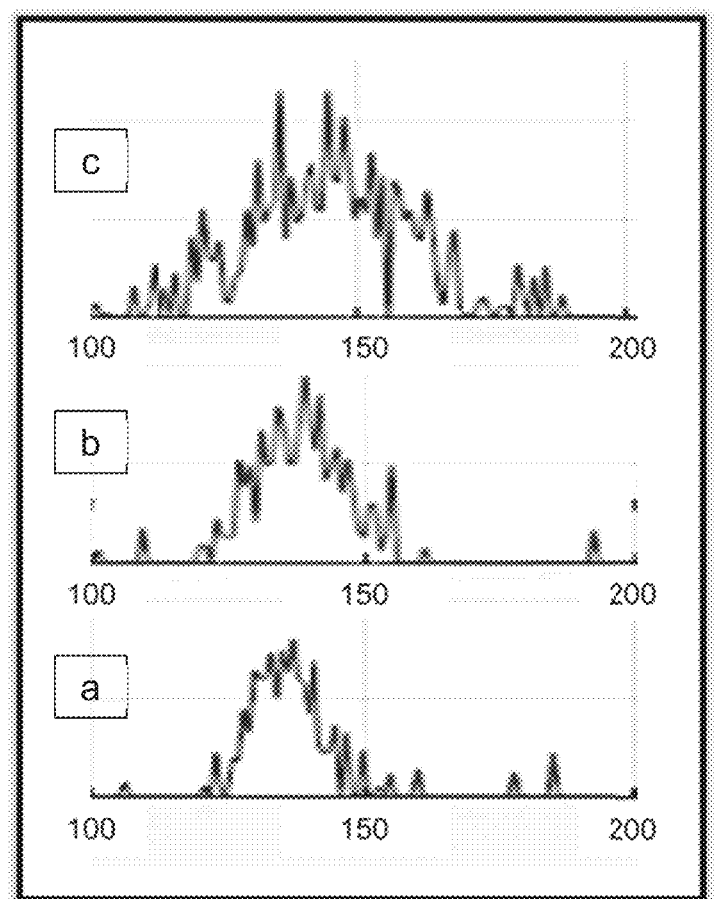
FIG. 10B shows three profiles of differential optical depth across the methane gas jet of FIG. 10A, corresponding to pixel values sampled along the lines labeled a, b, and c.

FIG. 10B shows cross-sectional profiles of the jet absorption image. The graphs plot differential optical depth vs. pixel number across a row of 512 pixels corresponding to the horizontal lines labeled a, b, c in FIG. 10A. It is apparent from these plots that the diameter of these absorption profiles is increasing along the jet axis, and that the turbulence creates fluctuations in absorption through the jet. The general shape of these plots is entirely consistent with the path length through a cross-section of a round jet in combination with a radial concentration profile of Gaussian shape. Superposed on this smooth theoretical profile are fluctuations in concentration due to turbulence.

The maximum of the absorption on each profile should occur on axis of the jet, if the imaging line-of-sight is perpendicular to the jet axis, as this is where the path length through the jet is a maximum and the gas concentration is largest. Based on the self-similar solution for turbulent round jets, the gas concentration on axis will decrease linearly along the jet as it expands, while the diameter increases linearly along the axis, and so the product of axial gas concentration with diameter should remain a constant, suggesting the column density along the jet axis should remain constant. However, due to the turbulent fluctuations, these profiles change over time, and so individual pixel values fluctuate. To cope with these turbulent fluctuations, it is suggested to use spatial averages of quantities across the jet, and then calculate the total absorption of a slice of jet, as it is due to the total mass of gas in that slice and not sensitive to the exact distribution of mass throughout the slice. Each row of pixels along consecutive cross-sections through the jet corresponds to a constant thickness slice, and since the jet diameter varies linearly with axial distance, hence, the slice volume increases as the square of the axial distance. But since the gas concentration dilutes linearly with axial distance in a self-similar round jet, the mass of gas in constant thickness slices is expected to increase linearly with axial distance along the jet. That is, the gas at the front of a jet slice flows slower than the gas at the rear of the jet slice, causing mass to build up between slices of constant thickness. And since the mass of gas in slices increases linearly along the jet axis, so should the absorption due to that mass. Thus, the integrated differential optical depth across each cross-section of the jet image should increase linearly along the jet. Similarly, the jet width in the absorption image should increase linearly along the jet, where the jet boundary is determined by the noise in the background image. Integrating the absorption across jet cross-sections acts to smooth out the effect of turbulent fluctuations on gas concentration in the jet.

Figure 11A:
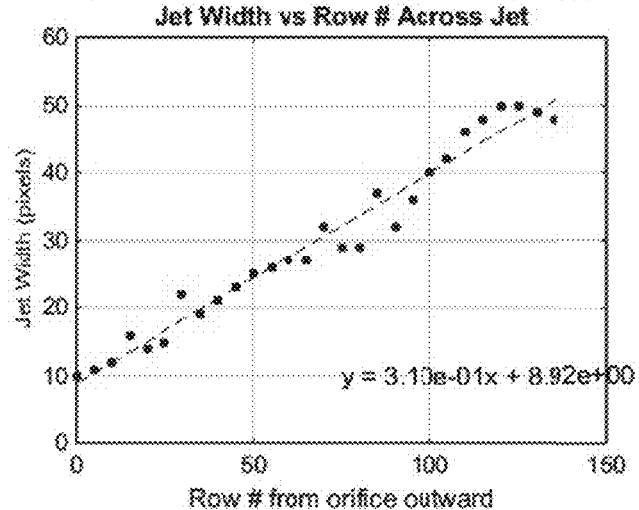
FIG. 11A shows a graph of the estimated jet width along the axis of the methane jet of FIG. 10A, and a least-squares linear regression to these data points.
Figure 11B:
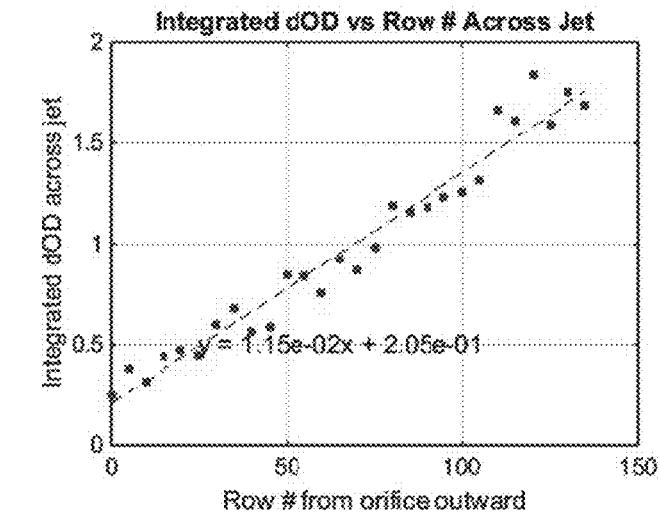
FIG. 11B shows a graph of the integrated differential optical depth across the width of the jet, along the axis of the methane jet of FIG. 10A, and a least-squares linear regression to these data points.
Figure 11C:
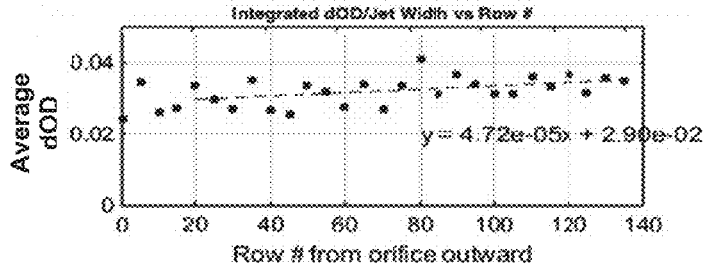
FIG. 11C shows a graph of the ratio of integrated differential optical depth to estimated jet width (i.e., the average differential optical depth) along the axis of the methane jet of FIG. 10A, and a least-squares linear regression to these data points.

FIGS. 11A and 11B plot the automatically extracted jet width and corresponding integrated differential optical depth (integrated-dOD), respectively, along the axial distance (approximately the image row number) for the jet image in FIG. 10A. It is apparent that both quantities follow clear linear trends, and so a least-squares regression line is fit to each quantity. Forming the ratio of integrated differential optical depth to jet width yields an average differential optical depth (Avg-dOD) value at each axial location along the jet. This ratio is plotted in FIG. 11C, to which a least-squares regression line is fit (starting away from the orifice to exclude the complex acoustic region just outside the hole). It is apparent from FIG. 11C that the slope of this regression line is very small, and that the intercept of the regression line then corresponds to the average differential optical depth extrapolated back to the effective orifice from which the gas leaks under pressure.

Figure 12:
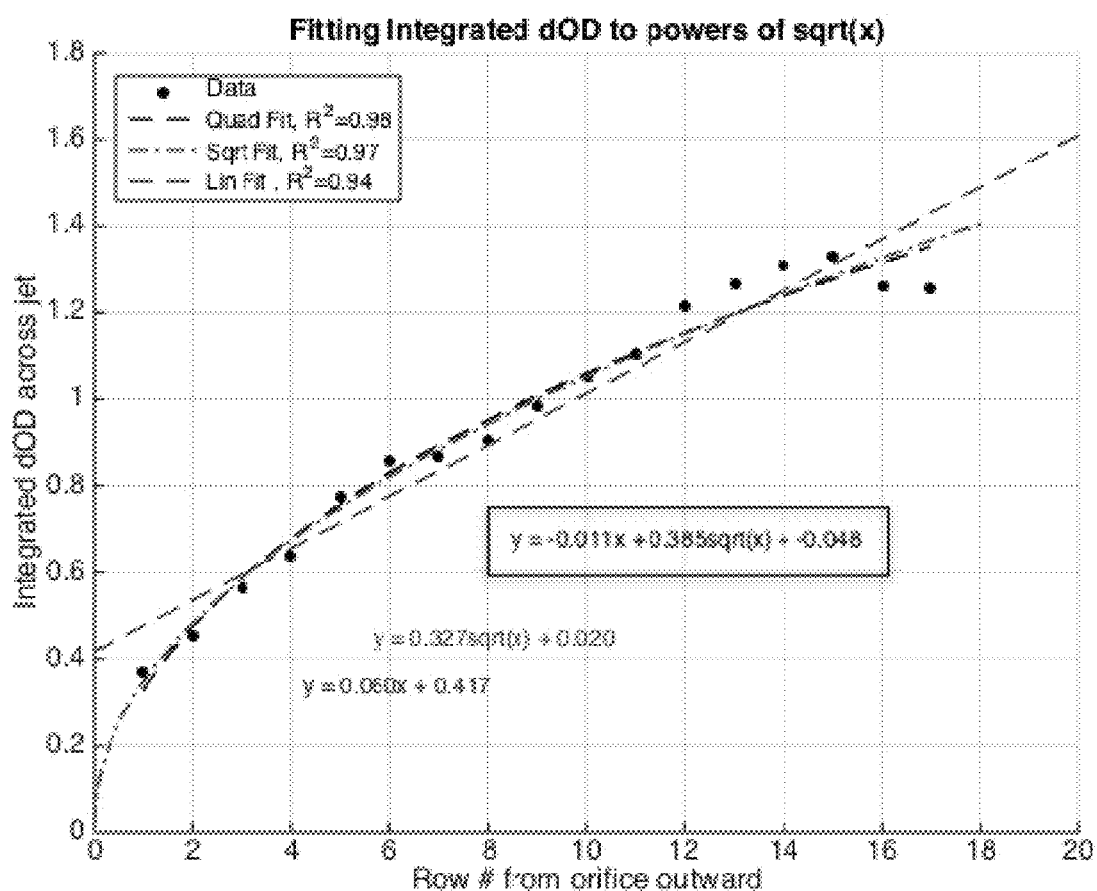
FIG. 12 shows a graph of the integrated differential optical depth across the width of a methane jet exiting a narrow slit (i.e., an idealized "crack") at a pressure of 60 psig.

FIG. 12 plots the integrated differential optical depth (integrated-dOD) along the axis of a natural gas jet emanating from a narrow (50 micron) slit orifice that is 1 cm long, meant to emulate a crack (instead of a hole) in a pressurized line at 60 psig. Following the same reasoning as above but for a plane turbulent jet (instead of a round turbulent jet), one finds that the integrated-dOD should scale with the square-root of the distance along the axis, as is apparent from the least-squares regression fits in FIG. 12. And since the integrated-dOD across a plane jet is independent of the orientation of the slit relative to the line-of-sight of the sensor, one can use this square-root versus linear behavior to distinguish between a gas leak emanating from a crack or a hole.

Absorption and Mass Flow Across a Range of Pressures and Orifice Sizes

Experiments have been conducted to image the release of methane gas under a range of pressures (50-1400 psig) exiting from round orifices (diameters of 0.75 mm and 1.0 mm). Gas jet boundaries are automatically extracted from the imagery, and the average differential optical depth (Avg-dOD) along the jet axis is computed. Fitting a least-squares regression line to this data determines the intercept of this regression line, which indicates the degree of absorption of the methane at the effective orifice.

Figure 13A:
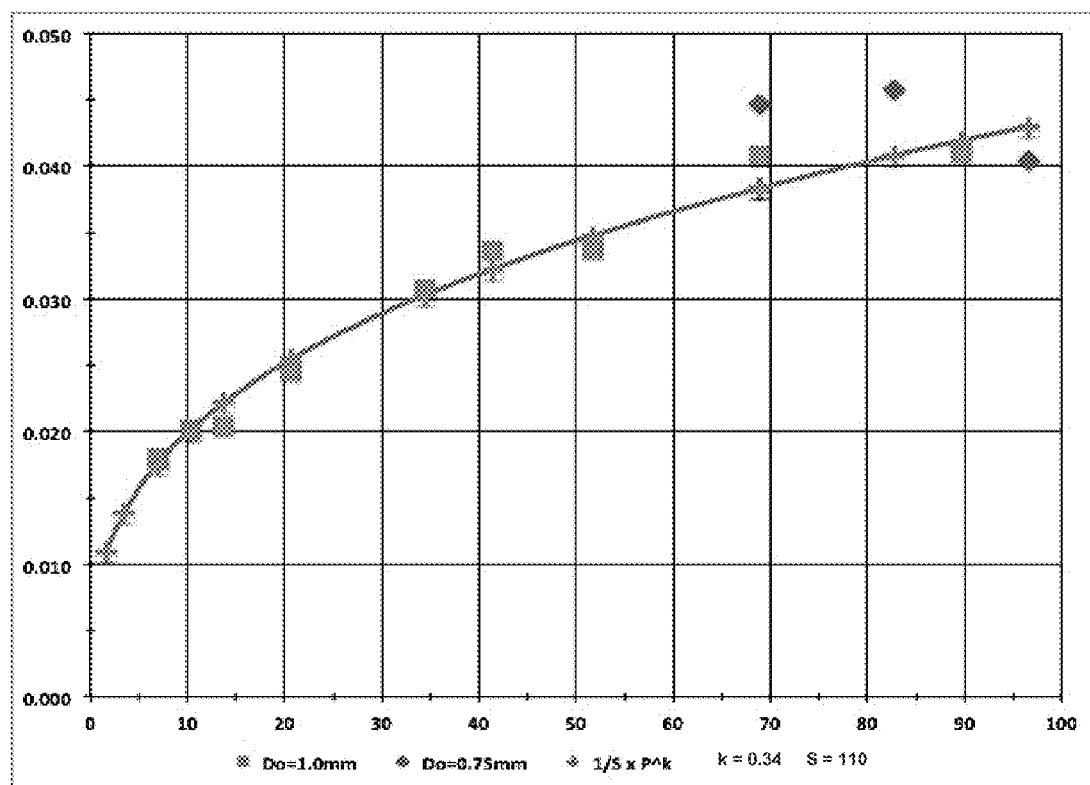
FIG. 13A illustrates for a set of experiments, a graph of the intercept value of average differential optical depth relative to the diameter of the leak hole vs. the internal pressure (in Bar) driving a methane jet from orifices of 1 mm and 0.75 mm, and compares the data to a smooth power-law curve.

FIG. 13A plots the value of this Avg-dOD intercept (scaled by orifice diameter) against the internal pressure P (in units of Bar, where 1 Bar=14.5 psi, the atmospheric pressure at sea level) for round orifices of 1 mm and 0.75 mm. The data points are consistent with a power-law behavior of pressure, for which the scaling constant and exponent values are shown on the graph. This is expected since the absorption by the methane gas at the effective exit hole (extrapolating back from the linear boundaries of the jet) will be proportional to the product of the effective orifice diameter and the local gas density, while the gas density is proportional to a power-law of the pressure through the adiabatic equation of state using the ratio of heat capacities for methane. Further experiments will determine the general utility of this specific power-law relationship across a range of orifice diameters and (approximately round) shapes.

Figure 13B:
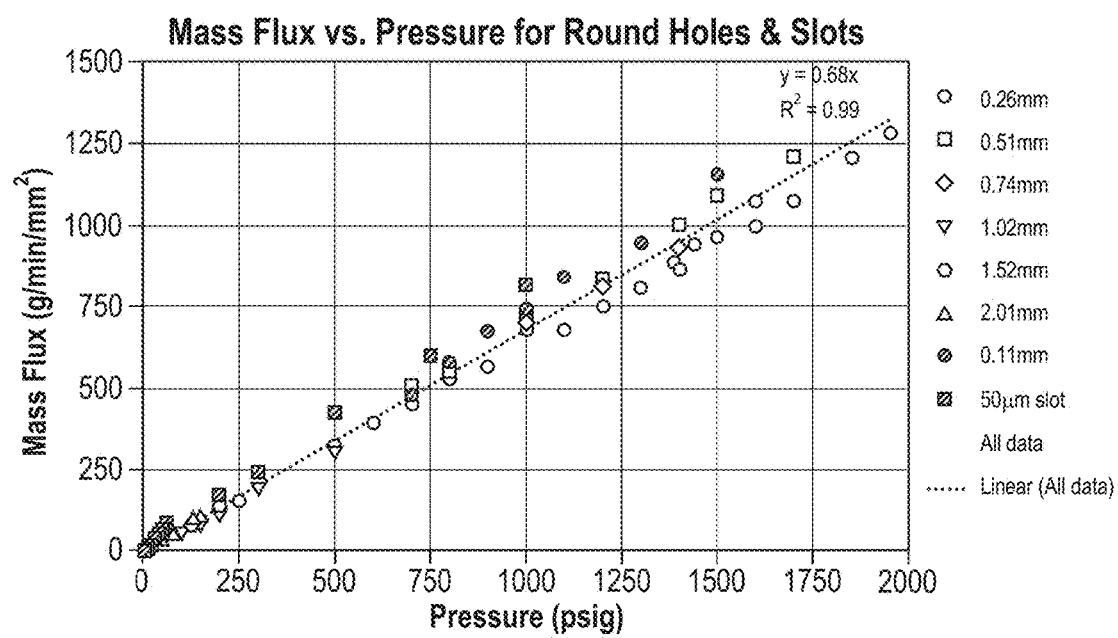
FIG. 13B illustrates for an extensive set of experiments including round and slit orifices of various sizes, a graph of the measured mass flux of methane (in grams per minute per unit area of the hole) vs. the internal pressure (in psig) driving the methane jet, and a least-squares linear fit to the data.

FIG. 13B plots the measured methane mass flow per orifice area (in grams/sec, divided by orifice area) against internal pressure for numerous experiments using round and slit orifices of different sizes. It is clear they follow the expected linear relationship, with a slope determined by the data. The mass flow out of the orifice is proportional to the product of the area of the orifice and the methane gas density in the pipe (which is proportional to the pressure in the pipe). Thus, while the Avg-dOD intercept curve scales linearly with effective diameter of a round orifice (as implied by FIG. 13A), the mass flow scales like the square of the effective diameter of a round orifice (as implied by FIG. 13B). These relationships taken together are therefore used to estimate the orifice size and mass flow of gas directly from the observed absorption image of a gas jet leaking from a hole under known internal pressure. Thus, it is possible to estimate the size of a leak hole directly from a gas jet absorption image, even if the leak hole itself is not visible in the image. And this leads directly to a leak rate or mass flow estimate. Similar relationships apply to a planar gas jet leaking from a narrow crack.

Figure 14A:
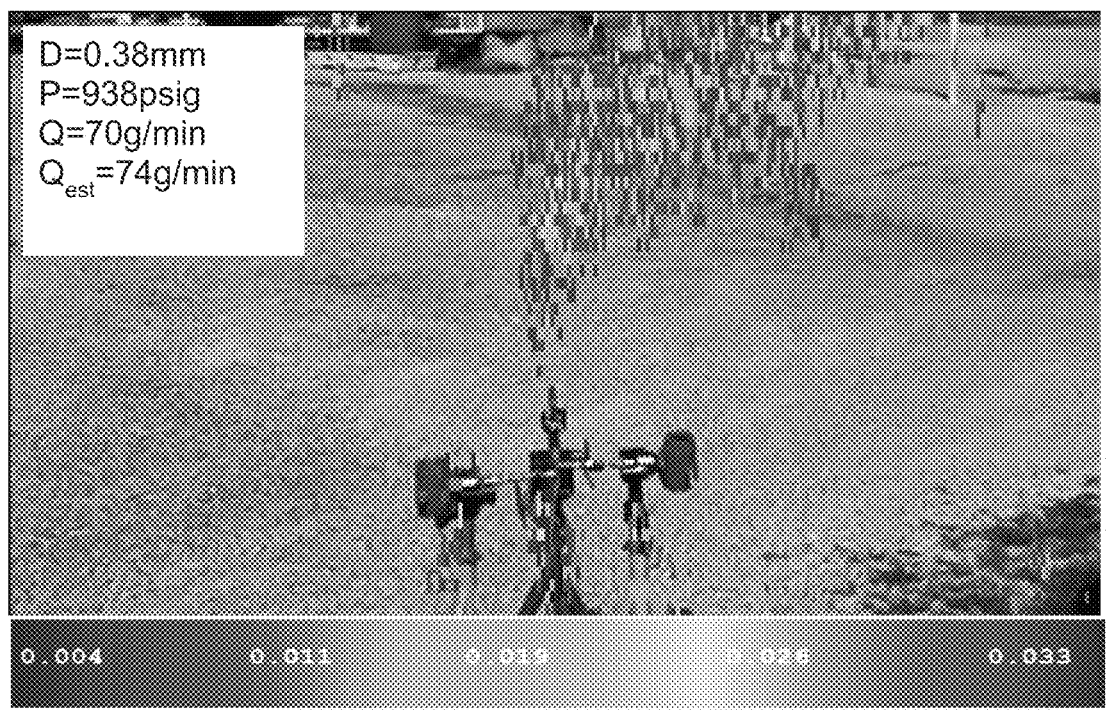
FIG. 14A shows an example gas absorption image for a field test of 100% methane exiting a 0.38 mm round orifice at an exit pressure of 938 psig in wind.

FIG. 14A shows an example gas absorption image of 100% methane exiting from a 0.38 mm round orifice at an exit pressures of 938 psig in wind. Experiments were conducted outdoors in natural sunlight under varying crosswinds. The instrumented mass flow was measured as 70 grams/minute of methane. The mass flow estimated directly from the imagery using the invented methods is 74 grams/minute.

Figure 14B:
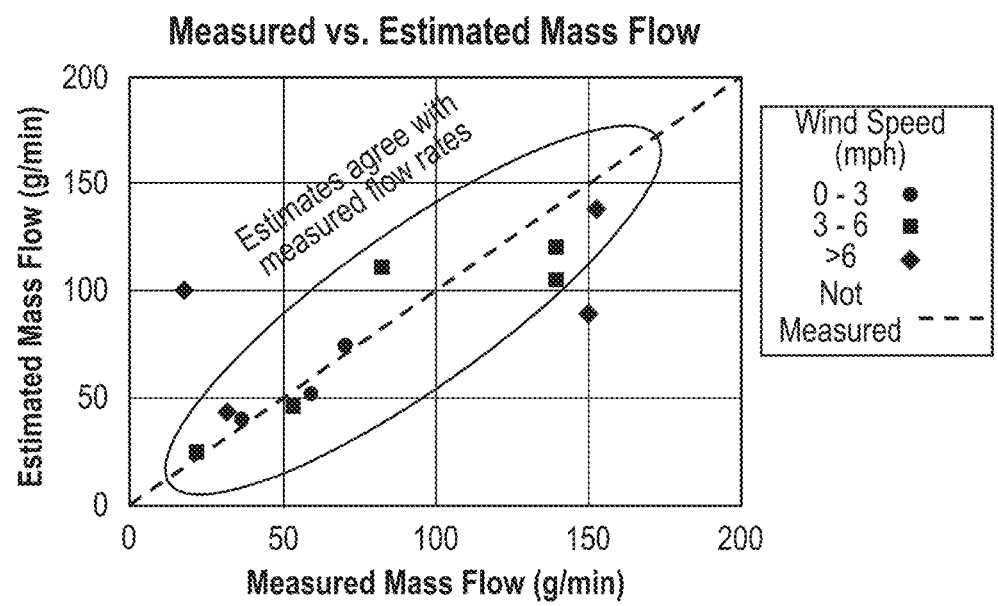
FIG. 14B compares image-based estimates of methane mass outflow to instrumented measurements of methane mass inflow, for a set of experiments conducted with round-hole orifices at various exit pressures up to 1000 psig, in winds measured between 0-10 miles/hour.

FIG. 14B graphs the data obtained using the setup in FIG. 14A. Specifically, FIG. 14B compares imagery estimated methane mass flows to instrumented measurements for a set of experiments conducted with round-hole orifices at various exit pressures, in winds measured between 0-10 miles per hour. Mass flow estimates are shown to agree well with instrumented "ground truth" measurements as taken up to 150 grams/minute. Data is presented for winds of 0-3 mph, 3-6 mph, and >6 mph. This validates the method for estimating gas leak rate from absorption imagery, for holes in pressurized lines.

Figure 15A:
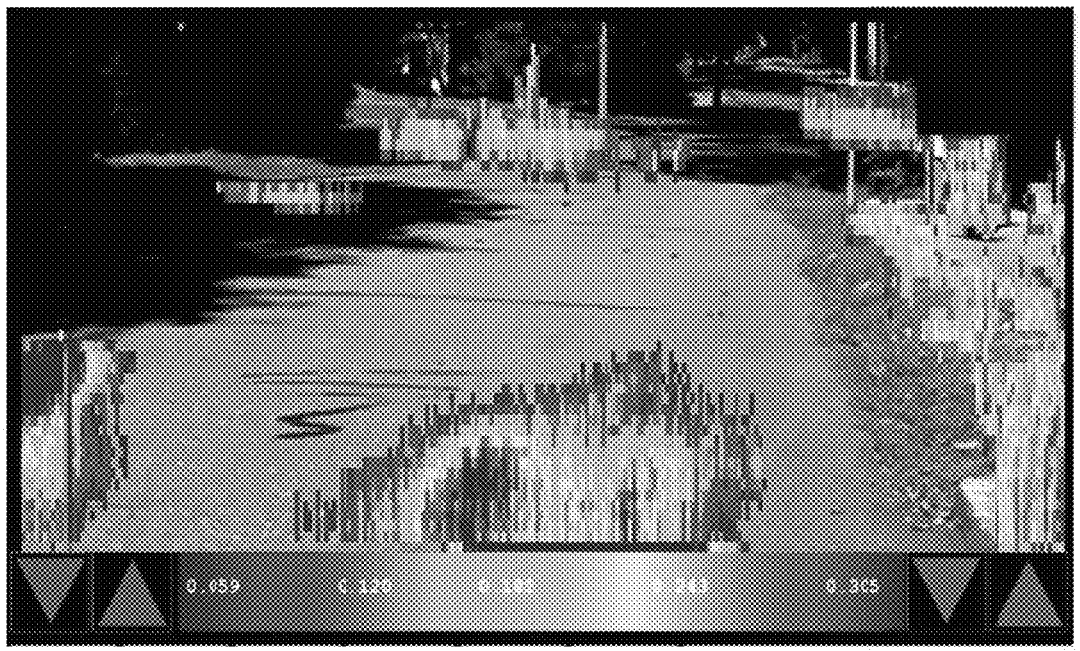
FIG. 15A shows an example gas absorption image of a residential street in the Boston area.

An example of gas imaging is shown in FIG. 15A, where natural gas is leaking from an underground pipe in municipal gas infrastructure in Boston, Mass. Gas emissions due to a leak in the underground pipeline are detected and overlaid on the background visible image. All detections as illustrated were confirmed using a flame ionization gas sensor to sample the air above each surface emission area. By the time the gas percolates up through the soil, it is approximately the same temperature as the ground itself. A sensor system such as presently disclosed can image the gas emissions from the surface in sunlight as shown, or alternatively using artificial illumination (possibly mixed with sunlight) from above reflecting off the ground, which is absorbed as it passes through the gas twice. FIG. 15A illustrates the patchy nature of ground surface emissions, with gas emerging from manholes, storm gratings, cracks in road asphalt and concrete sidewalks, as well as along the side of the road where the asphalt meets dirt and grass. All of these surface emissions may be due to a single leak in a pipe at the bottom of the hill near the end of the street. The spatial distribution of surface leak patches can be useful in bounding the actual leak location in the underground pipe.

Figure 15B:
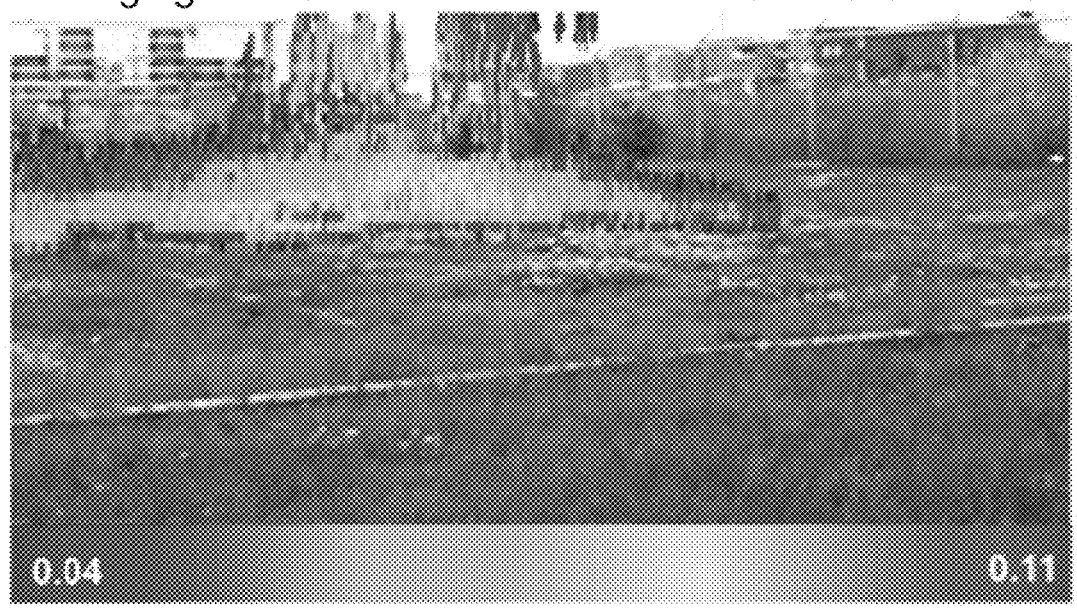
FIG. 15B shows an example absorption image of natural gas leaking from a small pipe at 4 feet below the surface of a field.

FIG. 15B shows an example absorption image of natural gas leaking from a small pipe at 4 feet below the surface of a field. The pipe is fed by the Montreal municipal gas network pressurized to 60 psig. The location of maximum surface emission is clear from the color overlay of gas absorption, and was confirmed using a gas sniffer.

Figure 16A:
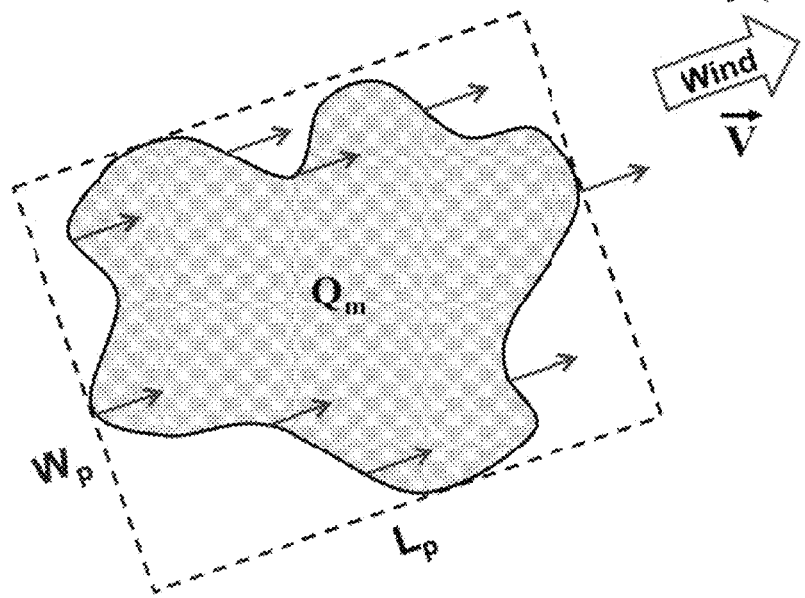
FIG. 16A illustrates a plan view of a surface patch emitting methane (or natural gas) at rate $Q_m$ grams/sec on average within its irregular boundary with ground-level winds of speed V.

A plan view of a surface patch emitting methane (or natural gas) at rate $Q_m$ grams/sec on average within an irregular boundary is shown in FIG. 16A. Ground-level winds, of speed V in the direction shown, determine the orientation of the bounding rectangular of dimensions $L_p$ along the wind direction and $W_p$ across the wind direction. In steady winds, the emission flux up from the ground balances the flux of methane flowing across the downwind boundary.

Figure 16B:
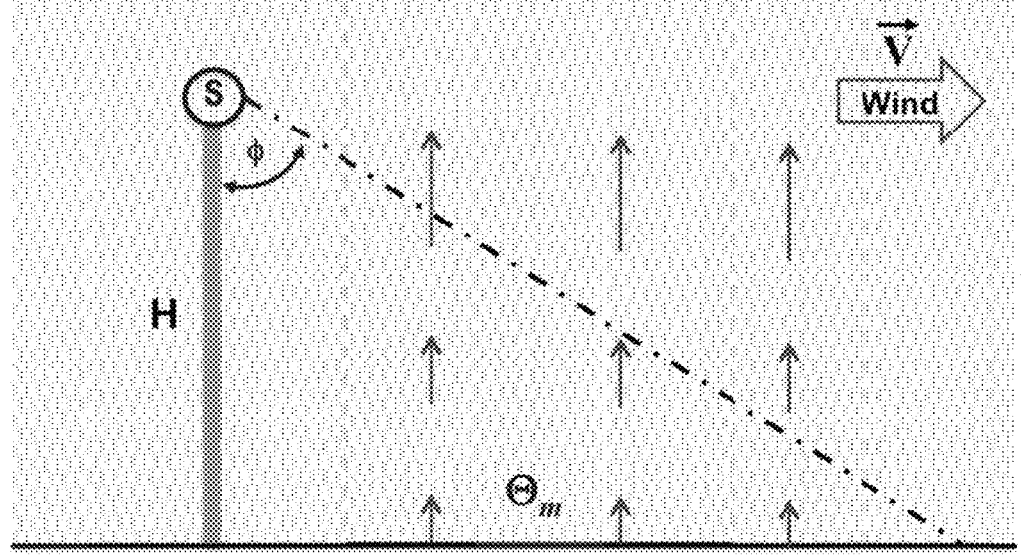
FIG. 16B illustrates a side view of the sensor S mounted atop a mast on the ground within a wide-area surface emission site.

FIG. 16B illustrates a side view of the sensor S mounted atop a mast on the ground within a wide-area surface emission site. The methane flux $\Theta_m$ (per unit area) out of the ground establishes a stratified methane atmosphere above the ground, wherein this emission flux balances the buoyancy driven upward flow of methane.

Next, the mathematical formulation of absorption imaging and quantification of gas leaks is described, using methane or natural gas as a specific example.

Defining the SWIR Spectral Bands

Spectral data is collected through multiple filters, each of bandwidth approximately 100 nm with transmission greater than 5%, spanning the wavelength region approximately 1950-2500 nanometers (i.e., 1.95-2.50 microns). This data provides coverage of spectral features that characterize methane, ethane, propane, butane, carbon dioxide, ammonia, and possibly other gases of interest, yet avoids the strong water vapor absorption features, as illustrated in FIG. 1A. The data is organized into multiple spectral bands, for example five bands as illustrated in FIG. 1B. The data itself is collected in real-time by the SWIR sensor as it points in directions in space that correspond to locations on the ground, or objects on the site, being monitored by the scanning SWIR sensor. In terms of spatial patterns, the data corresponds to one of several possible scan patterns including raster-scanned imagery over a prescribed field-of-view.

One of the multiple spectral bands is selected to include only weak or no features of the gases of interest, and is referred to as the "reference band," as exemplified by the 100 nm wide band centered near 2100 nm in FIG. 1B. Refer to this spectral band filter as the Reference Filter with transmission $F_{ref}(\lambda)$ and integrated transmission $F_{ref}$.

The other spectral band filters are simply referred to as Spectral Filter B (where B is the band number), each with transmission $F_B(\lambda)$, and integrated transmission $F_B$.

Data collected at each spectral band will be corrected for the integrated transmission associated with its corresponding spectral filter $F_B$, to form $I_B$ the intensity in band B. The intensity of each band is then measured relative to $I_{ref}$, the data collected at the reference band corrected by the transmission of the reference filter $F_{ref}$. The resulting transmission corrected data are a set of spectral band ratios forming a spectral pattern $P_B$ (a vector) defined as:

$$P_B = \text{Set of Band Ratios}\{I_B/I_{ref}\} \quad \text{(Eq. 1)}$$

Each gas of interest is characterized by its own spectral pattern of band ratios, and will be detected in the measured data by spectral pattern recognition methods, including spectral pattern unmixing in the case of gas mixtures. It can be shown that the 5-element spectral patterns associated with the gases shown in FIG. 1B enable separation of the gases of interest, including mixtures that characterize natural gas from geographically different locations and from processed distribution gas. Separation of pure methane from distribution gas is the most challenging, as distribution gas is typically 95% methane. It can be shown that even they can be separated up to noise levels that are 10% on average. The selection of spectral bands can be tailored to speciate and not confuse a desired set of gases and mixtures, or group together numerous gases (e.g., heavy hydrocarbons) to be recognized as a gas within the group.

Adapting the Sensor to the Ambient Environment

Denote the optical depths in each spectral band B, including the reference band, as measured in the ambient environment as $\tau_B^{(a)}$ and $\tau_{ref}^{(a)}$.

They are the products of the absorptivity and r, the path length through the environment. The band intensities resulting from the radiative transfer are:

$$I_B^{(a)} = S_B(r) Q_B F_B R_B \exp{-[\tau_B^{(a)}]} \quad \text{(Eq. 2a)}$$

$$I_{ref}^{(a)} = S_{ref}(r) Q_{ref} F_{ref} R_{ref} \exp{-[\tau_{ref}^{(a)}]} \quad \text{(Eq. 2b)}$$

Here, $S_B$ is the illumination source function (combining both solar and artificial illumination), $Q_B$ is the quantum efficiency of the detector, $F_B$ is the integrated transmission of the filter, and $R_B$ is the reflectance of the background material (which can be a calibration panel or the natural surrounding materials), all corresponding to spectral band B and similarly for the reference band.

Form the pattern $P_B$ of spectral band ratios, and note the spectral illumination source function ratio $S_B/S_{ref}$ is independent of path length r and only a function of wavelength.

Define the cross-channel gain $G_B$, ambient spectral differential absorption coefficient $\delta\alpha_B^{(a)}$ and path length $L_R$ from sensor to a reflector panel. Then, form the ration of Eq. 2a and Eq. 2b to obtain:

$$\frac{I_B^{(a)}}{I_{ref}^{(a)}} = \frac{[S_B(0) Q_B F_B R_B]}{[S_{ref}(0) Q_{ref} F_{ref} R_{ref}]} \exp{-[\tau_B^{(a)} - \tau_{ref}^{(a)}]} \quad \text{(Eq. 3a)}$$

$$\frac{I_B^{(a)}}{I_{ref}^{(a)}} = G_B \exp{-2L_R[\alpha_B^{(a)} - \alpha_{ref}^{(a)}]} = G_B \exp{-2L_R[\delta\alpha_B^{(a)}]} \quad \text{(Eq. 3b)}$$

where $$\frac{[S_B(0) Q_B F_B R_B]}{[S_{ref}(0) Q_{ref} F_{ref} R_{ref}]}$$

of Eq. 3a is corresponds to $G_B$ of Eq. 3b, and $[\tau_B^{(a)} - \tau_{ref}^{(a)}]$ of Eq. 3a corresponds to $2L_R[\delta\alpha_B^{(a)}]$ of Eq. 3b.

The SWIR illumination bouncing off a calibration reflector panel (an example of which is Spectralon) is measured in each spectral band B at two distances, the spot or image average intensities are calculated, and the log of their ratio is formed to solve for the unknowns $G_B$ and $\delta\alpha_B^{(a)}$ (or use more than two distances and solve for the unknowns via least squares).

Each gain $G_B$, as defined in Eq. 3B, incorporates the ratios of filter band transmissions, detector quantum efficiencies, and band reflectivities of the calibration panel. Each gain $G_B$ is rescaled (utilizing in-scene background reflectors) by the ratio of in-scene band reflectivities. $\delta\alpha_B^{(a)}$ and spectral samples of the in-scene background materials (cement, asphalt, dirt, grass, etc.) are used to determine the rescaled gain $G_B$ for each reflecting material. It is desired, but not essential, that the sensor automatically recognize the background materials that comprise a site being inspected or monitored.

Detecting and Imaging Gas Leaks

The sensor system samples or images in the direction of a possible gas leak of extent $D_J$ (e.g., jet width) and measures/senses the range $L_R$ to the reflecting surface in the background (either the reflector panel or in-scene material serving as a reflector).

Let $\tau_B^{(g+a)}$ be the band-B optical depth of the combined possible gas jet in the ambient environment from the sensor to the reflector at $L_R$ and back to the sensor. Then the intensities in the bands (including reference band) are:

$$I_B^{(g)} = S_B(r) Q_B F_B R_B \exp{-[\tau_B^{(g+a)}]} \quad \text{(Eq. 4a)}$$

$$I_{ref}^{(g)} = S_{ref}(r) Q_{ref} F_{ref} R_{ref} \exp{-[\tau_{ref}^{(g+a)}]} \quad \text{(Eq. 4b)}$$

Form each ratio of spectral band intensities, substitute the expression for the cross-channel gain (rescaled for background surface reflector), define the differential spectral absorption coefficient of gas $\delta\alpha_B^{(a)}$ and rearrange terms:

$$\frac{I_B^{(g)}}{I_{ref}^{(g)}} = G_B \exp{-\{2D_J[\delta\alpha_B^{(g)} - \delta\alpha_{ref}^{(a)}] + 2L_R[\delta\alpha_B^{(a)}]\}} \quad \text{(Eq. 5)}$$

Define the Excess Differential Spectral Absorptivity of the gas leak (for example, diluted natural gas) over that of the ambient atmosphere environment:

$$\Delta_B^{(g-a)} \equiv \delta\alpha_B^{(g)} - \delta\alpha_B^{(a)} = [\alpha_B^{(g)} - \alpha_{ref}^{(g)}] - [\alpha_B^{(a)} - \alpha_{ref}^{(a)}] \quad \text{(Eq. 6)}$$

So the Differential Spectral Optical Depth image due to the gas leak is obtained from the measured spectral intensities and calibration parameters:

$$\delta OD_B = [\Delta_B^{(g-a)}] D_J = -\frac{1}{2} \ln\left[\frac{1}{G_B} \frac{I_B^{(g)}}{I_{ref}^{(g)}}\right] - [\delta\alpha_B^{(a)}] L_R \quad \text{(Eq. 7a)}$$

In the case of negligible atmospheric absorption over range 2r compared to the gas leak itself, the $2^{nd}$ term on the right can be neglected, yielding:

$$\delta OD_B = -\frac{1}{2} \ln\left[\frac{1}{G_B} \frac{I_B^{(g)}}{I_{ref}^{(g)}}\right] \quad \text{(Eq. 7b)}$$

The factor of ½ comes from the double path length through the gas due to reflection of incident light off the background at range r. In the case of single pass transmission (e.g., sunlight through the gas), this factor is dropped.

Estimating Jet Mass, Orifice Size and Methane Mass Flux for Pressurized Leaks

Use the differential spectral optical depth image for a detected jet (or plume or cloud), compute the average $\delta OD_B$ across the profiles along its axis z, and sum along the axis to obtain total spectral optical depth of the gas.

$$\delta OD_B^{(jet)} = \Sigma_{axis} D_J(z) \overline{\delta OD_B}(z) \quad \text{(Eq. 8)}$$

Relate $\delta OD_B$ to column density to obtain total number of methane molecules (or other detected species), multiply by the mass of a methane (or other detected species) molecule to obtain total mass of gas in the jet (or plume or cloud).

$$\text{Mass}_{CH_4} = \left[\frac{\delta OD_B^{(jet)}}{\sigma_B - \sigma_{ref}}\right] m_{CH_4} \quad \text{(Eq. 9)}$$

Using the differential spectral optical depth sensed along the axis of a detected jet, derive the average-$\delta OD_B$ linear fit intercept, and combine this with the following power law equation that was discussed previously (see FIGS. 11C, 12, and 13A), $$\delta OD_{B0} = \frac{1}{S} D_O P^k \quad \text{(Eq. 10a)}$$

Solve Eq. 10a for (round) hole diameter $D_O$ and use the scale factor and exponent from the experimental data in FIG. 13A (rescaling pressure from psig to Bar) and find, $$D_O = S \frac{\overline{\delta OD_{B0}}}{P^k} \cong 110 \frac{\overline{dOD_0}}{(P/14.7)^{0.34}} \quad \text{(Eq. 10b)}$$

This result enables us to estimate the mass flow rate (g/min) from the hole by utilizing the orifice flow data fit equation of FIG. 13B, $$Q_m = \frac{\pi}{4} D_O^2 (0.68 P) \cong 0.53 D_O^2 P \quad \text{(Eq. 11)}$$

This mass flow estimate is valid for P above 1.8 Bar (~27 psi), so the flow is chocked (i.e., critical) at the orifice, with outflow at the local sound speed.

The units of the above quantities are:
Differential spectral optical depth $\delta OD_B$ is dimensionless
Round-hole diameter $D_O$ in mm
Pressure (interior or inline) P in psig
Mass flux $Q_m$ in grams/min Relationships equivalent to Eqs. 10b and 11 can be written among these quantities if expressed in units other than those used here. There are many systems of physical units that are customary in different countries and regions of the world.

Methane Mass Flux from Surface Patch Emissions Under Steady Winds

As shown in FIG. 16A, a surface patch by definition is isolated, surrounded by ambient clear air, with winds that are steady in direction and speed V. Gas emerges from the ground (or a tank), diffuses into the air above, and rises (methane) or falls/lingers (for heavier hydrocarbons) due to buoyancy forces. The wind convects the gas downwind as it continues to disperse and rise.

The mass of methane associated with a surface patch is estimated from spectral imaging, which provides the differential spectral optical depth of methane over the entire patch. Therefore, one can sum the pixels over the entire patch, similar to Eq. 8 for a gas jet, and convert the result to total methane mass over the patch, analogous to Eq. 9.

Measure the wind direction and speed V near ground/surface level, and assume it is representative of the wind at the emitting surface patch. Also measure range from the sensor to the surface patch, so that pixel angular dimensions in the image of the patch can be converted to linear dimensions.

The vertical flux of methane due to buoyancy is generally negligible compared to the horizontal mass flux due to a mild wind as it crosses the patch. The steady wind V (cm/sec) blows methane across the patch and away, as it diffuses out of the ground into the air above the patch. Thus, an equilibrium is established in which the surface emission mass flux $Q_m$ is balanced by the windblown mass crossing the downwind boundary of the patch. This enables us to estimate the surface emission mass flux of methane.

The shallow methane diffusion layer above the surface patch has a characteristic thickness D and concentration c, which give rise to the measured differential optical depth $\delta OD_B$ at each pixel. Select a threshold for the optical depth at a desired level to delineate the boundaries of the patch. Construct the bounding rectangle around that patch, such that one axis of the rectangle aligns with the wind direction, as illustrated in FIG. 16A. Using the range measured to the patch, convert the pixel dimensions of this bounding rectangle to linear dimensions L×W (cm). The volume flux (cm³/sec) across the downwind boundary of the patch is equivalent to the volume flux DWV across side W of the bounding rectangle. The methane mass flux $Q_m$ (grams/sec) is obtained from the product of methane concentration in the diffusion layer, methane mass density at standard temperature and pressure (STP), and volume flux across the downwind boundary;

$$Q_m = c\rho_{CH_4} DWV \quad \text{(Eq. 12a)}$$

Expressing $c\rho_{CH_4} D$ in terms of the differential spectral optical depth $\delta OD_B$, obtain the estimate of methane mass flux from a surface patch in a steady wind:

$$Q_m = \left[\frac{m}{\sigma_B - \sigma_{ref}}\right]_{CH_4} WV(\delta OD_B) \quad \text{(Eq. 12b)}$$

Methane Mass Flux from Surface Patch Emissions Under Gusting Winds

As shown in FIG. 16A, this assumes each surface patch (or tank vent) is isolated, surrounded by ambient clear atmosphere, with winds that are gusting, whereas the result in Eq. 12b assumes winds that are steady. The methane emerges from the ground (or vent), diffuses into the air above, and rises due to buoyancy forces. Heavier hydrocarbons will fall (or linger) due to negative (or neutral) buoyancy. However, when a gust occurs, the wind rapidly blows the entire layer of methane (or heavier gas) away from the surface patch.

In gusting winds, the methane layer above the patch alternates between building itself up by diffusion out of the surface (in steady winds of speed V) and being rapidly destroyed by a sudden gust of wind. This allows the build-up of a methane layer to be observed over time. Thus, the increase of methane mass above the patch is due to the surface emission mass flux $Q_m$, minus the mass flux due to transport by a steady wind V as in Eq.12B:

$$\frac{dM_{CH_4}}{dt} = Q_m - \left[\frac{m}{\sigma_B - \sigma_{ref}}\right]_{CH_4} WV(\delta OD_B) \quad \text{(Eq. 13a)}$$

Direct observation of the accumulation of methane is possible by imaging the time-varying differential optical depth over the patch, since $$\left[\frac{dM_{CH_4}}{dt}\right]_{obs} = A_p \rho_{CH_4} \frac{d}{dt}(cD) = \left[\frac{m}{\sigma_B - \sigma_{ref}}\right]_{CH_4} A_p \frac{d}{dt}(\delta OD_B) \quad \text{(Eq. 13b)}$$

$A_p$ is the area of the patch (or vent) observed before the gust, D is the changing thickness of the methane layer above the patch, and c is the increasing concentration of methane as the diffusion layer grows until the next gust.

Equating expressions Eq.13a and Eq.13b, we obtain an estimate of the methane mass flux $Q_m$ (grams/time) from a surface patch (or vent) in gusting wind, by observing the time-varying differential optical depth as the methane layer is reestablished under steady wind conditions;

$$Q_m = \left[\frac{m}{\sigma_B - \sigma_{ref}}\right]_{CH_4} \left\{ A_p \frac{d}{dt}(\delta OD_B) + WV(\delta OD_B) \right\} \quad \text{(Eq. 13c)}$$

Methane Mass Flux from Wide-Area Surface Emissions

FIG. 16B illustrates the geometry of monitoring wide-area surface emissions, where the sensor itself is located within or next to the area of interest. Examples include landfills, open face mine pits on land, and tailing ponds where the surface is water. Methane is released from materials at or below the surface, and is emitted across a wide surface area. In this scenario, the effects of buoyancy in vertical mass transport outweigh the effects of horizontal winds.

Although surface emissions can be non-uniform, horizontal winds only serve to mix the diluted methane layer so as to become horizontally more uniform as it rises above the surface. The horizontal winds do not generate a net source or sink of methane (except at the distant downwind boundary of the area). The methane forms a vertically stratified atmosphere, diluted by air, rising due to positive buoyancy and possible vertical convective air currents. Strong convective currents reduce the vertical stratification, leading to a nearly uniform concentration over the wide-area surface.

An equilibrium is established in which the surface emission flux (grams per time per unit area) sustains the vertical methane-in-air atmosphere. The sensor can measure the differential spectral optical depth between the sensor and the surface (for SWIR reflective surfaces like ground, but not water). Alternatively, the sensor can measure the optical depth between the sensor and a boundary of the emitting area by sensing horizontally or upwards, with the sun (or an illuminator) transmitting through the methane atmosphere. An illuminator can also be located on a platform at a distance from the sensor, with the light transmitting through the methane atmosphere towards the sensor. For example, this type of probing of an extensive methane-in-air atmosphere can be accomplished by tracking the sun over an open-pit mine or over a tailings pond, in order to estimate the vertical methane flux, as is of interest in the Canadian oil sands.

Consider the sensing geometry as shown in FIG. 16B, with the sensor at height H above the emitting surface, tilted downwards at an angle $\phi$. The path length through the stratified methane layer to the surface is $H/\cos(\phi)$. The sensor can be mounted on a mast or on an overlook, or flying above the surface sensing downwards. It is required that the optical path through the methane atmosphere not be optically thick (optical depth less than approximately 3) so that the sensor receives sufficient signal from light reflected off the surface.

The vertical flux of methane mass per unit surface area $\Theta_m$ is constant with height above the surface z, as methane mass is conserved as it rises in steady state:

$$\Theta_m = \Theta_m(0) = \Theta_m(Z) = \rho_{CH_4} c(z) v_z(z) \quad \text{(Eq. 14)}$$

where $c(z)$ is the methane concentration profile and $v_z(z)$ is the vertical velocity profile of the rising methane.

The vertical velocity profile is due primarily to the buoyancy force as the methane gas displaces the heavier air around it, where the air is in hydrostatic equilibrium and exerts downward pressure on the surface. As methane gas rises, it gains speed under gravity g according to, $$\frac{\partial v_z}{\partial t} = -\left[\frac{\rho_{CH_4} - \rho_a}{\rho_a}\right] g = -\left[\frac{\Delta \rho}{\rho_a}\right] g \quad \text{(Eq. 15a)}$$

where $\Delta \rho$ is the reduced density of methane relative to its ambient surroundings. If we neglect second-order effects associated with methane rising through an atmosphere of already reduced density (due to the presence of low concentration methane mixed with air), we can treat the ambient density as approximately the density of clear air itself near the surface, and treat it as constant. Integrate Eq.15a over time to obtain the velocity and position following a gaseous element as it rises, and solve for the vertical velocity field as a function of height, as the methane atmosphere is assumed to be in a steady state.

$$v_z(t) = -\left[\frac{\Delta \rho}{\rho_a}\right] gt \quad \text{(Eq. 15b)}$$

$$z(t) = -1/2 \left[\frac{\Delta \rho}{\rho_a}\right] gt^2 \quad \text{(Eq. 15c)}$$

$$v_z(z) = \sqrt{2\left[\frac{-\Delta \rho}{\rho_a}\right] g} \; (z^{1/2}) \quad \text{(Eq. 15d)}$$

Substitute Eq.15d into Eq.14 to obtain the vertical mass flux per area:

$$\Theta_m = \rho_{CH_4} \sqrt{2\left[\frac{-\Delta \rho}{\rho_a}\right] g} \; [z^{1/2} c(z)] \quad \text{(Eq. 16a)}$$

Since the vertical mass flux must be constant with height, Eq.16a implies that the methane concentration profile above the surface must vary inversely with height according to $$c(z) = c_o \left[\frac{z_o}{z}\right]^{1/2} \quad \text{(Eq. 16b)}$$

where $c_o$ and $z_o$ correspond to the concentration at height $z_o$ just above the surface diffusion layer where buoyancy dominates over diffusion. The methane profile of Eq.16b is induced by buoyancy alone, it is not applicable inside the shallow diffusion layer where height z tends towards zero (i.e., there is no singularity as z approaches 0).

Substitute Eq.16b into Eq.16a to obtain the vertical mass flux per unit area, $$\Theta_m = \rho_{CH_4} \sqrt{2\left[\frac{-\Delta\rho}{\rho_a}\right]g} \, [z_o^{1/2} c_o] \quad \text{(Eq. 16c)}$$

Relate the differential spectral optical depth $\delta OD_B$ to the integral of concentration profile along the optical path from sensor to surface. The sensor can be calibrated to the prevailing sunlight reflecting off the surface, or it can utilize a SWIR illuminator mounted near the sensor (and double the optical path length). Accounting for the slant range through the methane atmosphere due to sensor tilt-angle $\phi$, and noting that $z_o \ll H$, we obtain $$\delta OD_B(\phi) = \frac{1}{\cos(\phi)}\left[\frac{\sigma_B - \sigma_{ref}}{m}\right]_{CH_4} \rho_{CH_4} \int_0^H c(z)dz \quad \text{(Eq. 17a)}$$

$$= \frac{2}{\cos(\phi)}\left[\frac{\sigma_B - \sigma_{ref}}{m}\right]_{CH_4} \rho_{CH_4} [z_o^{1/2} c_o] \sqrt{H} \quad \text{(Eq. 17b)}$$

Eq.17b suggests the $\phi$-dependence of optical depth is $1/\cos(\phi)$, so can be averaged across tilt-angle measurements and inverted to obtain, $$[z_0^{1/2} c_o] = 1 \Big/ 2\left[\frac{m}{\sigma_B - \sigma_{ref}}\right]_{CH_4} \frac{1}{\rho_{CH_4}} \frac{1}{\sqrt{H}} \langle \cos(\phi)[\delta OD_B(\phi)]\rangle \quad \text{(Eq. 17c)}$$

where the angle brackets imply averaging across tilt-varying sensor data, to provide an estimate of the differential spectral optical depth straight below ($\phi=0$) the sensor at height H, denoted as $\delta OD_B{}^{\downarrow}$.

Combining Eq.17c with Eq.16c yields the formula to estimate vertical methane mass flux per unit area for wide-area surface emissions from sensor data. Adopting the following units for quantities $\Theta_m$ (grams/sec/cm²), $\sigma$ (cm²), H (meters), and $m_{CH_4}$ (grams), obtain the vertical mass flux per unit area due to wide-area surface emissions:

$$\Theta_m = \sqrt{\frac{1}{2}\left[\frac{\rho_a - \rho_{CH_4}}{\rho_a}\right]g} \left[\frac{m}{\sigma_B - \sigma_{ref}}\right]_{CH_4} \frac{\delta OD_B^{\downarrow}}{\sqrt{H}} \quad \text{(Eq. 18a)}$$

$$= 1.5\left[\frac{m}{\sigma_B - \sigma_{ref}}\right]_{CH_4} \frac{\delta OD_B^{\downarrow}}{\sqrt{H}} \quad \text{(Eq. 18b)}$$

CONCLUSION, RAMIFICATIONS AND SCOPE

The embodiments as described above consist of both multispectral SWIR sensors and methods for rapidly detecting, localizing and imaging methane and other hydrocarbon gases, and methods to estimate the leak rate or mass flux. Multiple embodiments of sensor systems have been described to enable imaging of gas leaks, and multiple methods have been disclosed for estimating methane mass flux from holes in pressurized lines, from surface patch emissions due to underground gas pipe leaks, and from wide-area surface emissions. Example imagery and leak rate estimates across a wide variety of conditions illustrate the viability of the sensors and methods.

Summarizing the advantages of the invention over existing alternative gas imaging technologies, we note the ability to image and quantify gas leaks using natural sunlight without the need for any thermal contrast between the gas and the background, the ability to image and quantify methane in the presence of water vapor and fog, and the ability to quantify leak rates and surface emission flux in order to assess leak severity, prioritize repairs, and monitor emissions over extended periods of time. These capabilities have application in gas safety, gas leak inspection, and greenhouse gas emissions monitoring.

While the above description contains much specificity, these should not be construed as limitations on the scope, but rather as exemplification of several embodiments thereof. Many other variations are possible. For example, by selecting the appropriate spectral filters in the SWIR, the invention can be used for detecting and quantifying other gases, liquids, emulsions, powders, and solids, in addition to the ones cited above and discussed in detail. Thus, multiple spectral filters can be selected to detect ammonia gas, which is both combustible and toxic. Also fertilizers can be detected and quantified, as can soil wetness and general plant health, thus other embodiments may be well suited for agricultural assessments. Yet other embodiments can be constructed that are well suited for detection of ammonium nitrate and its variants as used in the making of homemade explosives. Additionally, the methods developed for leak rate quantification of gases can be utilized for detecting gases and other substances in other spectral bands, in addition to the SWIR band. Accordingly, the scope should be determined not by the embodiments illustrated, but by the appended claims and legal equivalents.

The foregoing description has been directed to particular embodiments. However, other variations and modifications may be made to the described embodiments, with the attainment of some or all of their advantages. It will be further appreciated by those of ordinary skill in the art that modifications to the above-described systems and methods may be made without departing from the concepts disclosed herein. Accordingly, the invention should not be viewed as limited by the disclosed embodiments. Furthermore, various features of the described embodiments may be used without the corresponding use of other features. Thus, this description should be read as merely illustrative of various principles, and not in limitation of the invention.

Many changes in the details, materials, and arrangement of parts and steps, herein described and illustrated, can be made by those skilled in the art in light of teachings contained hereinabove. Accordingly, it will be understood that the following claims are not to be limited to the embodiments disclosed herein and can include practices other than those specifically described, and are to be interpreted as broadly as allowed under the law.

What is claimed is:

1. A method for characterizing the mass flow of hydrocarbon gas emissions of a hydrocarbon of interest from an aperture or surface, the hydrocarbon of interest being at a substantially known or measured pressure prior to being emitted from the aperture or surface, the method comprising:
   a. obtaining a differential absorption image of the gas emissions using a multispectral imaging sensor comprising
      i. plural discrete photo-detectors, each responsive to light in a wavelength range of 1.0 to 2.6 microns, each photo-detector having a respective electronic read-out circuit for providing respective outputs, ii. plural spectral filters, each spectral filter substantially covering a respective photo-detector and being transmissive to light of wavelengths spanned by a spectral feature of a hydrocarbon compound of interest,
iii. an optical element for gathering and focusing incident illumination at least in a wavelength range of 1.0 to 2.6 microns through each of the plural spectral filters and onto the respective discrete photo-detector for the discrete photo-detectors to sense the filtered incident illumination;
iv. a scanning actuator for causing the incident illumination to be received in a two-dimensional scan pattern,
v. at least one signal integration and conversion circuit in communication with the read-out circuits for selectively integrating, amplifying, and digitizing the read-out circuit outputs,
vi. at least one scan control circuit in communication with the scanning actuator for controlling the scanning actuator and the at least one signal integration and conversion circuit for generating, by the at least one signal integration and conversion circuit, a sequence of two-dimensional data elements from the integrated, amplified, and digitized read-out circuit outputs for each of multiple spectral bands in coordination with the scan pattern, and
vii. a processor in communication with the at least one signal integration and conversion circuit for
  I. receiving the generated data elements and a value representative of a distance between the photo-detectors and a reflective calibration target for calibrating the data elements of each spectral band relative to data elements associated with a spectral feature of a hydrocarbon compound of interest, by determining calibration parameters comprising
    a). a dark level offset for each spectral band,
    b). a relative gain for data elements of interest between spectral bands, and
    c). a relative absorption coefficient for each spectral band characterizing the local atmosphere across multiple spectral bands, and
  II. adapting the relative gain across spectral bands, using the generated data elements and the calibration parameters, to spectral reflectivities of background materials within the environment, and determining a differential optical depth among spectral bands for assessing absorption by hydrocarbons along said scan pattern; and
b. estimating the diameter of a substantially round aperture from which the hydrocarbon gas is emitted or the mass flow rate of said hydrocarbon of interest based upon at least one of i. a relationship between the average differential optical depth along the gas jet extrapolated to the vertex of the gas jet and the substantially known or measured pressure with respect to the diameter or area of the aperture from which the hydrocarbon gas is emitted,
ii. a relationship between the substantially known or measured pressure and the mass flow of the hydrocarbon gas emitted from the aperture of inferred diameter or area,
iii. a relationship between the differential optical depth and the mass flow per unit area of the hydrocarbon gas emitted from a surface of limited extent under a substantially steady wind of measured speed and direction,
iv. a relationship between the differential optical depth, a rate of change of the differential optical depth, and a mass flow per unit area of the hydrocarbon gas emitted from the surface of limited extent under a substantially steady wind of measured speed and direction following a wind gust, and
v. a relationship between the differential optical depth derived at a height H above a wide-area surface from which the hydrocarbon gas is emitted and the mass flow per unit area of the hydrocarbon gas emitted from the surface under the influence of buoyancy.

2. The method of claim 1, wherein the spectral feature of the hydrocarbon of interest is at least ten nanometers.

3. The method of claim 1, wherein the transmissive wavelengths of each spectral filter do not overlap with the transmissive wavelengths of other filters.

4. The method of claim 1, wherein the scanning actuator is selected from the group consisting of resonant oscillating mirrors, galvanometric driven mirrors, rotating multi-faceted mirrors, electrically actuated micro-mirror arrays, electrically controlled rotation stages, and a dual-axis pan-tilt unit, to scan at least in two perpendicular directions.

5. The method of claim 1, wherein the at least one scan control circuit is in communication with the scanning actuator to cause the incident illumination to be received from a two-dimensional scan pattern selected from the group consisting of open scan paths, closed scan paths, and raster scan paths.

6. The method of claim 1, further comprising a frame for physically maintaining the plural spectral filters with respect to the plural discrete photo-detectors, whereby light passes through each spectral filter before impinging upon the respective discrete photo-detector.

7. The method of claim 1, wherein the optical element comprises at least one of a lens, a curved mirror, and a diffractive surface.

* * * * *